(12) United States Patent
Nanchen et al.

(10) Patent No.: US 8,377,942 B2
(45) Date of Patent: Feb. 19, 2013

(54) ISOXAZOLINES DERIVATIVES AND THEIR USE AS PESTICIDE

(75) Inventors: Steve Nanchen, Basel (CH); Noëlle Gauvry, Kembs (FR); Francois Pautrat, Mulhouse (FR)

(73) Assignee: Novartis AG, Basel (CH)

( * ) Notice: Subject to any disclaimer, the term of this patent is extended or adjusted under 35 U.S.C. 154(b) by 59 days.

(21) Appl. No.: 13/133,432

(22) PCT Filed: Dec. 17, 2009

(86) PCT No.: PCT/EP2009/067437
§ 371 (c)(1),
(2), (4) Date: Jun. 8, 2011

(87) PCT Pub. No.: WO2010/079077
PCT Pub. Date: Jul. 15, 2010

(65) Prior Publication Data
US 2011/0245274 A1 Oct. 6, 2011

(30) Foreign Application Priority Data

Dec. 18, 2008 (EP) ..................................... 08172156

(51) Int. Cl.
*C07D 239/26* (2006.01)
*C07D 403/14* (2006.01)
*C07D 471/04* (2006.01)
*C07D 413/14* (2006.01)
*C07D 263/10* (2006.01)
*C07D 261/04* (2006.01)
*A61K 31/437* (2006.01)
*A61K 31/4402* (2006.01)
*A61K 31/4406* (2006.01)
*A61K 31/4409* (2006.01)
*A61K 31/421* (2006.01)
*A61K 31/422* (2006.01)

(52) U.S. Cl. ........ 514/256; 514/300; 514/340; 514/341; 514/374; 514/378; 544/333; 546/113; 546/272.1; 548/238; 548/240

(58) Field of Classification Search ........................ None
See application file for complete search history.

(56) References Cited

FOREIGN PATENT DOCUMENTS

| WO | WO 2007/075459 A2 | 7/2007 |
| WO | WO 2007/079162 A1 | 7/2007 |
| WO | WO 2008/154528 A2 | 12/2008 |

*Primary Examiner* — Joseph K. McKane
*Assistant Examiner* — Alicia L Otton
(74) *Attorney, Agent, or Firm* — Ann R. Pokalsky, Esq.; Dilworth & Barrese, LLP

(57) ABSTRACT

Novel isoxazoline compounds, compositions containing the compounds and methods for making the compounds are disclosed. The compounds and compositions have pesticidal properties and are suitable for controlling ectoparasites on non-human animals.

19 Claims, No Drawings

ISOXAZOLINES DERIVATIVES AND THEIR USE AS PESTICIDE

CROSS-REFERENCE TO RELATED APPLICATIONS

This application claims priority to PCT Application Number PCT/EP2009/067437, filed Dec. 17, 2009, which claims priority to EP Application Number 08172156.5, filed Dec. 18, 2008.

FIELD OF THE INVENTION

This invention relates to novel isoxazolines, their N-oxides and salts, processes for their manufacture, their use in the control of ectoparasites, especially insects and acari, on non-human animals, especially productive livestock and domestic animals, and furthermore pesticidal compositions which contain one or more of these compounds.

BACKGROUND OF THE INVENTION

PCT Patent Publication WO 2007/079162 discloses isoxazoline derivatives of Formula (A)

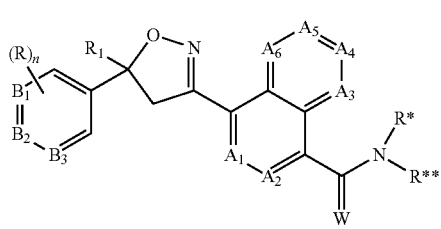

(A)

wherein, inter alia, each of $A_1$-$A_6$ and $B_1$-$B_3$ are $C(R_3)$, $R_1$ is haloalkyl and W is O or S. The compounds are mainly used in the control of invertebrate, pests in agronomic environments. Many products are commercially available for these purposes, but the need continues for new compounds that are more effective, less costly, less toxic, environmentally safer or have different modes of action. It now has been surprisingly found that novel naphthyl derivatives with a modified heterocyclic side chain have superior properties in the control of pests.

SUMMARY OF THE INVENTION

This present invention is directed to compound of formula (I)

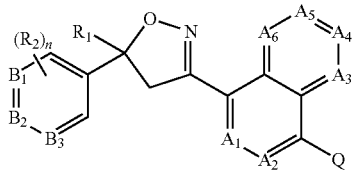

including all geometric and stereoisomers, N-oxides, and salts thereof, and compositions containing them and their use for controlling parasites, wherein $A_1$, $A_2$, $A_3$, $A_4$, $A_5$ and $A_6$ are each independently selected from the group consisting of $CR_3'$ and N;

n is an integer from 0 to 4;

$B_1$, $B_2$ and $B_3$ are each independently selected from the group consisting of $CR_2'$ and N;

each $R_2'$ is independently of the other H or $R_2'$, each $R_3'$ is independently of the other H or $R_3$;

$R_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently; selected from $R_4$;

each $R_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_2$-$C_6$ alkoxycarbonyl, cyano (—CN) or nitro (—$NO_2$);

each $R_3$ is independently halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$ alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$alkylamino, $C_1$-$C_6$alkoxycarbonyl, —CN or —$NO_2$;

$R_4$ is halogen, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkyl-sulfonyl, —CN or —$NO_2$;

Q is a 5- or 6-membered heterocyclic ring, or a $C_6$-$C_{10}$-carbocyclic ring system or a 8-, 9- or 10-membered fused hetero-bicyclic ring system, each of them being unsubstituted or substituted with one or more substituents independently selected from halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_3$-$C_6$-cycloalkoxy, $C_1$-$C_6$-haloalkoxy, $C_2$-$C_6$-alkenyl, $C_2$-$C_6$-haloalkenyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_5$-alkylsulfonyl, $C_1$-$C_6$-haloalkylsulfonyl, —CN, —$NO_2$, amino, N-mono- or N,N-di-$C_1$-$C_6$-alkylamino, $CO_2H$, $C_1$-$C_6$-alkoxycarbonyl, sulfonamido N-mono- or N,N,di-$C_1$-$C_6$-alkylsulfonamido, $CONH_2$, N-mono- or N,N,di-$C_1$-$C_6$-alkylamino-carbonyl, N-mono- or N,N,di-$C_1$-$C_6$-haloalkylaminocarbonyl, N—$C_1$-$C_2$-haloalkylamino-carbonyl-$C_1$-$C_2$-alkylaminocarbonyl, $C_1$-$C_6$-alkylcarbonylamino, $C_2$-$C_6$-alkanoyl, $C_2$-$C_6$-halo-alkanoyl, $CH_2R_5$, a group C(O)N=CHN($CH_3$)$_2$, a group C(O)N=CHNOCH$_3$, pyrrolidonyl-carbonyl, and unsubstituted or halogen-, $C_1$-$C_6$-alkyl-, $C_1$-$C_6$-haloalkyl-, $C_1$-$C_6$-alkoxy-, $C_1$-$C_5$-haloalkoxy-, nitro- or cyano-substituted phenyl, benzyl, phenethyl, pyridyl, pyridinylmethyl, pyrimidinyl, pyrimidinylmethyl, benzoyl or phenoxy; and $R_6$ is $CO_2H$, $C_1$-$C_6$-alkoxycarbonyl, $CONH_2$, N-mono- or N,N,di-$C_1$-$C_6$-alkylaminocarbonyl, N-mono- or N,N,di-$C_1$-$C_6$-haloalkylaminocarbonyl, $C_1$-$C_6$-alkylcarbonylamino, pyridinylaminocarbonyl or tetrahydrofuranyl.

According to a preferred embodiment there is provided a compound of formula (I) above, wherein $A_1$, $A_2$, $A_3$, $A_4$, $A_5$ and $A_6$ are each independently selected from the group consisting of $CR_3'$ and N;

n is an integer from 0 to 4;

$B_1$, $B_2$ and $B_3$ are each in selected from the group consisting of $CR_3'$ and N;

each $R_2'$ is independently of the other H or $R_2$; each $R_3'$ is independently of the other H or $R_3$;

$R_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently selected from $R_4$;

each $R_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$- haloalkylsulfonyl, N-mono- or N,N-di-$C_1$-$C_6$-alkylamino, $C_2$-$C_6$ alkoxycarbonyl, cyano (—CN) or nitro (—$NO_2$);

each $R_3$ is independently halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$ alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$-alkylamino, $C_2$-$C_6$-alkoxycarbonyl, —CN or —$NO_2$;

$R_4$ is halogen, $C_1$-$C_6$-alkoxy, $C_1$-$C_6$-alkylthio, $C_1$-$C_6$-alkylsulfinyl, $C_1$-$C_6$-alkyl-sulfonyl, —CN or —$NO_2$; and Q is a 5- or 6-membered heterocyclic ring, or a $C_6$-$C_{10}$-carbocyclic ring system or a 8-, 9- or 10-membered fused hetero-bicyclic ring system, each of them being unsubstituted or substituted with one or more substituents independently selected from halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkyl-sulfonyl, $C_1$-$C_6$-haloalkylsulfonyl, —CN, —$NO_2$, amino, N-mono- or N,N-di-$C_1$-$C_6$-alkylamino, $C_2$-$C_6$alkoxylcarbonyl, sulfonamide, N-mono- or N,N,di-$C_1$-$C_6$-alkylsulfonamido, N-mono- or N,N-di-$C_1$-$C_6$-alkylocarbonylamino, $C_2$-$C_6$-alkanoyl and unsubstituted or halogen-, $C_1$-$C_6$-alkyl-, $C_1$-$C_6$-haloalkyl-, $C_1$-$C_6$-alkoxy-, $C_1$-$C_6$-haloalkoxy-, nitro- or cyano-substituted phenyl, benzyl, benzoyl or phenoxy.

This invention also provides a composition comprising a compound of formula (I), a N-oxide or a salt thereof, and at least one additional component selected from the group consisting of a surfactant, a solid diluent and a liquid diluent.

In one embodiment, this invention also provides a composition for controlling parasites, in particular ectoparasites, comprising a biologically effective amount of a compound of formula (I), an N-oxide or a salt thereof, and at least one additional component selected from the group consisting of a surfactant, a solid diluent and a liquid diluent, said composition optionally further comprising a biologically effective amount of at least one additional biologically active compound or agent.

This invention further provides the composition described above in the form of a bait composition wherein the solid diluent and/or the liquid diluent comprises one or more food materials, said composition optionally comprising an attractant and/or a humectant.

This invention further provides a trap device for controlling parasites, in particular ectoparasites, comprising said bait composition and a housing adapted to receive said bait composition, wherein the housing has at least one opening sized to permit the parasites to pass through the opening so the invertebrate pest can gain access to said bait composition from a location outside the housing, and wherein the housing is further adapted to be placed in or near a locus of potential or known activity for the parasites pest.

This invention also provides a method for controlling parasites comprising contacting the parasites or their environment with a biologically effective amount of a compound of formula (I), an N-oxide or a salt thereof, (e.g., as a composition described herein). This invention also relates to such method wherein the parasites or their environment are contacted with a composition comprising a biologically effective amount of a compound of formula (I), an N-oxide or a salt thereof, and at least one additional component selected from the group consisting of a surfactant, a solid diluent and a liquid diluent, said composition optionally further comprising a biologically effective amount of at least one additional biologically active compound or agent.

This invention also provides a composition for protecting an animal from an parasitic pest comprising a parasiticidally effective amount of a compound of formula (I) an N-oxide or a salt thereof, and at least one carrier. The present invention further provides the composition described above in a form for oral administration. This invention also provides a method for protecting an animal from a parasitic pest comprising administering to the animal a parasiticidally effective amount of a compound of formula (I), N-oxide or a salt thereof.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

"Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl.

"Alkynyl" includes straight-chain or branched alkynes such as ethynyl, 1-propynyl, 2-propynyl and the different butynyl, pentynyl and hexynyl isomers, "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)CHS(O)$— and the different butylsulfinyl, pentylsulfinyl and hexylsulfinyl isomers.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers.

"N-alkylamino", "N,N-di-alkyamino" and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S$ (O)—. Examples of "haloalkylsulfonyl" include $CF_3S(O)_2$—, $CCl_3S(O)_2$—, $CF_3CH_2S(O)_2$— and $CF_3CF_2S(O)_2$—.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3OC(=O)$—, $CH_3CH_2OC(=O)$, $CH_3CH_2CH_2OC(=O)$—, $(CH_3)_2CHOC(=O)$— and the different butoxy- or pentoxycarbonyl isomers, for example tert.-butoxycarbonyl (Boc).

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2.

"Aromatic" indicates that each of the ring atoms is essential in the same plane and has a p-orbital perpendicular to the ring plane, and in which (4n+2) π electrons, where n is a positive integer, are associated with the ring to comply with Hückel's rule.

The terms "heterocyclic ring" or "heterocycle" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

When Q is a 5 or 6-membered nitrogen-containing heterocyclic ring, may be attached to the remainder of formula (I) through any available carbon or nitrogen ring atom, unless otherwise described.

Each $R_2$ is independently of the other preferably halogen, $C_1$-$C_6$-haloalkyl, $C_1$-$C_6$ haloalkoxy or —CN, more preferably halogen, $CF_3$, $OCF_3$ or —CN, and in particular halogen.

$B_1$, $B_2$ and $B_3$ are each independently of the other preferred the group $CR_2'$, wherein $R_2'$ is H or $R_2$, and for $R_2$ the above-given meanings and preferences apply. $R_2'$ is most preferably H or halogen.

The variable n is meant to summarize all radicals $R_2$ in the 6-membered ring. n is preferably an integer from 0 to 4, more preferably from 1 to 3, and in particular 2 or 3.

$R_1$ is preferably $C_1$-$C_6$-alkyl optionally substituted with one or more substituents independently selected from more preferably $C_1$-$C_3$-alkyl optionally substituted with halogen, even more preferably $C_1$-$C_3$-haloalkyl, especially preferably $C_1$-$C_2$-alkyl substituted with F, and in particular $CF_3$.

Each $R_3$ is independently of the other preferably halogen, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N-mono- or N,N-di-$C_1$-$C_2$-alkylamino, —CN or —$NO_2$, more preferably halogen, $C_1$-$C_2$-alkyl, $C_1$-$C_2$-haloalkyl, cyclopropyl, $C_1$-$C_2$-alkoxy, —CN or —$NO_2$, and even more preferably halogen, $C_1$-$C_2$ alkyl, $C_1$-$C_2$ alkoxy, —CN or —$NO_2$.

$A_1$, $A_2$, $A_3$, $A_4$, $A_5$ and $A_6$ are each independently of the other preferably a group $CR_3'$. $R_3'$ is preferably H or $R_3$, wherein for $R_3$ the above-given meanings and preferences apply. Preferably, three of the radicals $A_1$, $A_2$, $A_3$, $A_4$, $A_5$ and $A_6$ are each CH and the other three radicals are either CH or $CR_3$. Most preferably, $A_1$, $A_2$, $A_3$, $A_4$, $A_5$ and $A_6$ are each CH.

$R_4$ is preferably halogen, $C_1$-$C_2$-alkyl, $C_1$-$C_2$-alkoxy, —CN or —$NO_2$, more preferably halogen, —CN or —$NO_2$, and in particular halogen.

According to one preferred embodiment of the invention, Q is a $C_6$-$C_{10}$-carbocyclic ring system, for example phenyl, naphthyl, tetrahydronaphthyl, indanyl, indenyl, hydrindanyl or octahydro-pentalen, in particular phenyl, which is each unsubstituted or substituted by one or more same or different substituents selected from the group of substituents as defined before for Q. Q is preferably phenyl which is substituted by 1 to 4, preferably 1 to 3 and in particular 1 or 2 same or different substituents selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkyl-sulfonyl, —CN, —$NO_2$, $C_1$-$C_4$-alkoxycarbonyl, sulfonamido, $C_2$-$C_3$-alkanoyl and unsubstituted or halogen-, $C_1$-$C_4$-alkyl-, $C_1$-$C_4$-haloalkyl-, $C_1$-$C_4$-alkoxy-, $C_1$-$C_4$-haloalkoxy-, nitro- or cyano-substituted phenyl, benzyl, benzoyl and phenoxy. Q is more preferably phenyl, which is substituted by 1 to 3, in particular 1 or 2, same or different substituents selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —$NO_2$, and unsubstituted or halogen-, $C_1$-$C_2$-alkyl-, $C_1$-$C_2$-haloalkyl-, $C_1$-$C_2$-alkoxy-, $C_1$-$C_2$-haloalkoxy-, nitro- or cyano-substituted phenyl or phenoxy.

According to another preferred embodiment of the invention, is a 5- or 6-membered heterocyclic ring, which may be saturated or preferably unsaturated, and which is unsubstituted or substituted with one or more substituents selected from the group of substituents as defined before for Q.

Preferred substituents of the heterocyclic ring Q are, for example, $C_1$-$C_4$-alkyl, $C_1$-$C_4$-halo-alkyl, $C_1$-$C_4$-alkoxy, $C_1$-$C_4$-haloalkoxy, $C_1$-$C_4$-alkylthio, $C_1$-$C_4$haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, —CN, —$NO_2$, $C_1$-$C_4$alkoxy-carbonyl, N-mono- or N,N-di-$C_1$-$C_4$-alkylcarbonylamino, sulfonamido, $C_2$-$C_3$-alkanoyl and unsubstituted or halogen- or $C_1$-$C_4$-alkyl-substituted phenyl, benzyl, benzoyl and phenoxy. Even more preferred substituents of the heterocyclic ring Q are selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —$NO_2$, and $C_1$-$C_4$-alkoxycarbonyl, in particular $C_1$-$C_2$-alkyl, $C_1$-$C_2$-haloalkyl, and $C_1$-$C_4$-alkoxycarbonyl.

A suitable heterocyclic ring is, for example, a 5 or 6-membered heteroaromatic ring having from 1 to 4, preferably from 1 to 3 same or different heteroatoms selected from the group consisting of N, O and S, which is further unsubstituted or substituted by one or more substituents as defined before for Q including the preferences given therefore. The heterocyclic radical Q is preferably substituted by 0 to 3, in particular 0, 1 or 2 substituents from the group as defined before for Q.

Examples of a 5 or 6-membered unsaturated aromatic heterocyclic ring optionally substituted with from one or more substituents include the rings Q-1 through Q-60 illustrated in Exhibit 1 wherein R is any substituent as defined before for Q including the preferences given, and r is an integer from 0 to 4, limited by the number of available positions on each Q group. As Q-28, Q-29, Q-35, Q-36, Q-37, Q-38, Q-39, Q-40, Q-41 and Q-42 have only one available position, for these Q groups r is limited to the integers 0 or 1, and r being 0 means that the Q group is unsubstituted and a hydrogen is present at the position indicated by (R)$_r$.
Exhibit 1
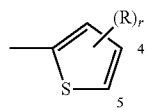
Q-1
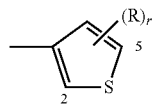
Q-2
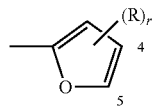
Q-3
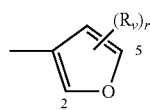
Q-4
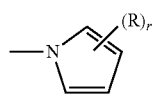
Q-5
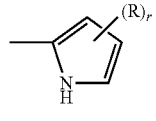
Q-6
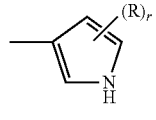
Q-7
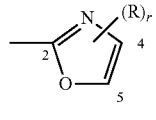
Q-8
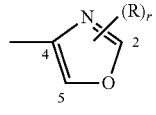
Q-9
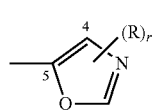
Q-10
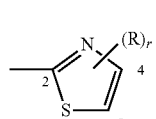
Q-11
-continued
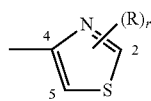
Q-12
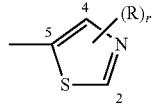
Q-13
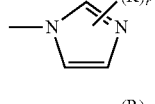
Q-14
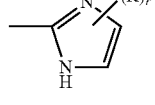
Q-15
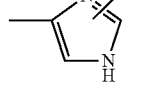
Q-16
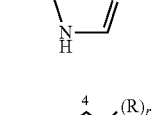
Q-17
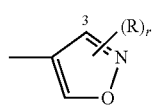
Q-18
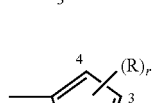
Q-19
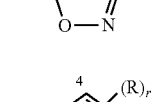
Q-20
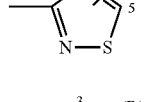
Q-21
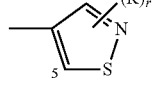
Q-22
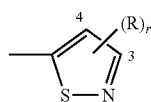
Q-23
Q-24

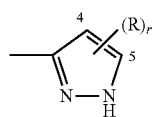 Q-25
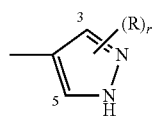 Q-26
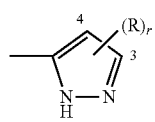 Q-27
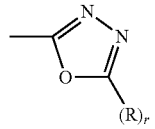 Q-28
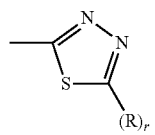 Q-29
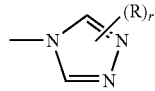 Q-30
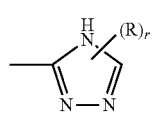 Q-31
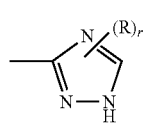 Q-32
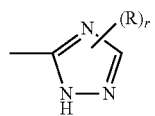 Q-33
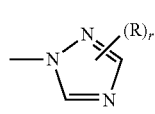 Q-34
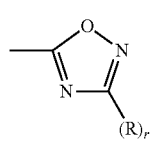 Q-35
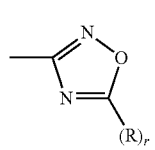 Q-36
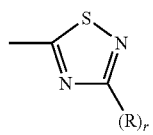 Q-37
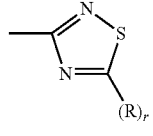 Q-38
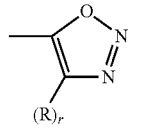 Q-39
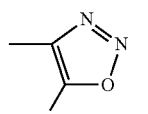 Q-40
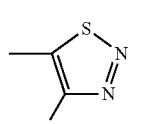 Q-41
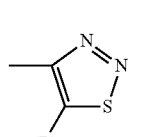 Q-42
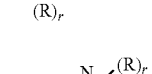 Q-43
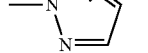 Q-44
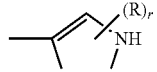 Q-45
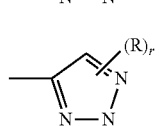 Q-46
 Q-47
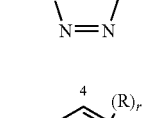 Q-48

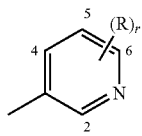

Q-49

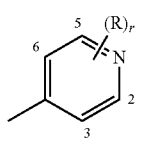

Q-50

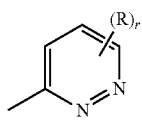

Q-51

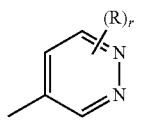

Q-52

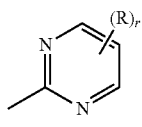

Q-53

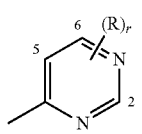

Q-54

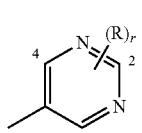

Q-55

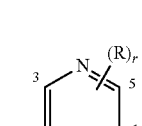

Q-56

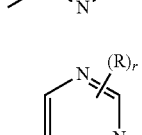

Q-57

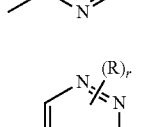

Q-58

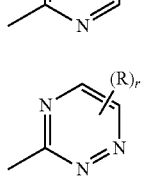

Q-59

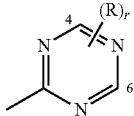

Q-60

A further group of suitable heterocyclic radicals comprises, for example, a 5- or 6-membered heteroaliphatic or partly unsaturated ring having from 1 to 4, preferably from 1 to 3 same or different heteroatoms selected from the group consisting of N, O and S, which is further unsubstituted or substituted by one or more substituents as defined before for Q including the preferences given therefore.

Examples of heteroaliphatic or partly unsaturated rings include the radicals illustrated in Exhibit 2 below, wherein R end r are as defined above including the preferences given.

Exhibit 2

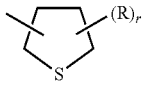

Q-61

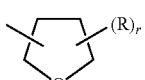

Q-62

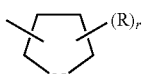

Q-63

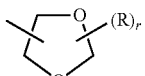

Q-64

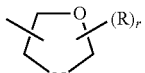

Q-65

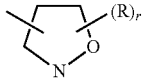

Q-66

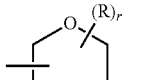

Q-67

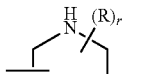

Q-68

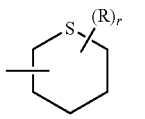

Q-69

| | |
|---|---|
| Q-70 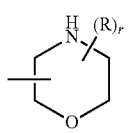 | Q-83 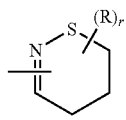 |
| Q-71 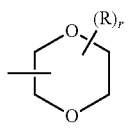 | Q-84 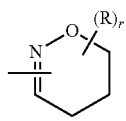 |
| Q-72 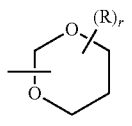 | Q-85 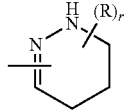 |
| Q-73 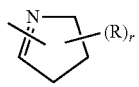 | Q-86 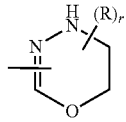 |
| Q-74 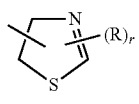 | Q-87 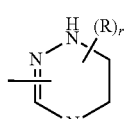 |
| Q-75 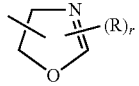 | Q-88 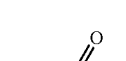 |
| Q-76 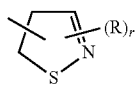 | Q-89 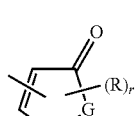 |
| Q-77 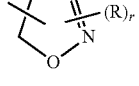 | Q-90 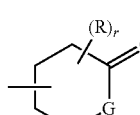 |
| Q-78 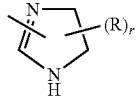 | Q-91 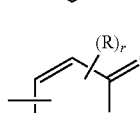 |
| Q-79 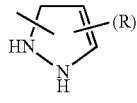 | Q-92 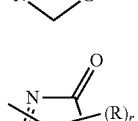 |
| Q-80 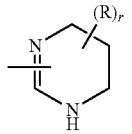 | Q-93 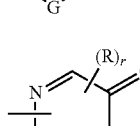 |
| Q-81 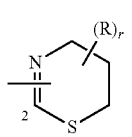 | Q-94 |
| Q-82 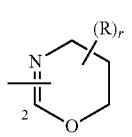 | |

-continued

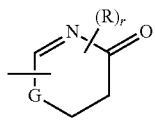   Q-95

A preferred heterocyclic radical Q is of formula

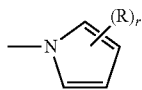   Q-5

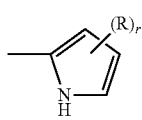   Q-6

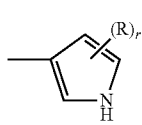   Q-7

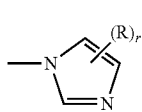   Q-14

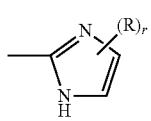  Q-15

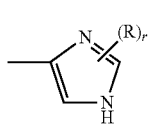  Q-16

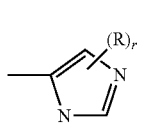  Q-17

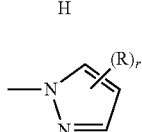  Q-24

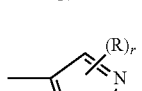  Q-26

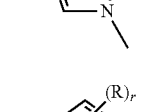  Q-30

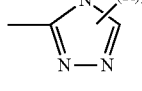  Q-31

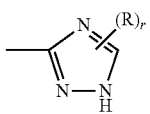  Q-32

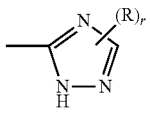  Q-33

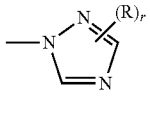  Q-34

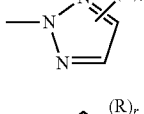  Q-43

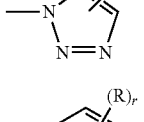  Q-47

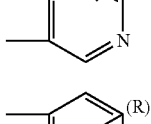  Q-49

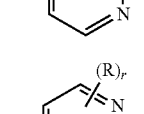  Q-50

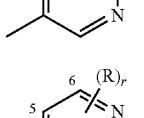  Q-52

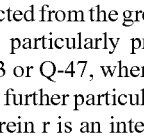  Q-54 wherein r is an integer from 0 to 3 and R is independently selected from the group given for Q including the preferences. Q is particularly preferred the unsubstituted radical Q-34, Q-43 or Q-47, wherein r is 0 in each case.

A further particularly preferred radical Q is a radical Q-44, wherein r is an integer from 0 to 3, in particular 1, and R is independently selected from the group given for Q including the preferences. Another preferred radical Q is a radical Q-75, wherein r is an integer from 0 to 3, in particular 1, and R is independently selected from the group given for Q including the preferences.

A further preferred radical Q is a radical Q-5, Q-14, Q-24, Q-25, Q-26, Q-30, Q-32, Q-34, Q-43, Q-44, Q-47, Q-49, Q-50 or Q-75, in particular a radical Q-24, Q-26, Q-30, Q-32, Q-34, Q-44 or Q-47, which is each unsubstituted or substituted by one or more substituents selected from the group consisting of $C_1$-$C_2$-alkyl, halo-$C_1$-$C_2$-alkyl, halo-$C_1$-$C_2$-alkylcarbonyl, cyano, $C_1$-$C_4$-alkoxycarbonyl, $C_1$-$C_4$-alkoxycarbonylmethyl, carboxy-$C_1$-$C_2$-alkyl, aminocarbonyl, N-mono- or N,N-di-$C_1$-$C_2$-alkylaminocarbonyl, halo-$C_1$-$C_2$-alkylaminocarbonylmethyl, halo-$C_1$-$C_2$-alkylaminocarbonylmethylaminocarbonyl, halovinyl, —C(O)N=CHN(CH$_3$)$_2$, —C(O)N=CHNHOCH$_3$, unsubstituted or halogen or C$_1$-C$_2$-alkoxy-substituted phenyl, benzyl and phenylethyl, unsubstituted and halogen-substituted 2-, 3- and 4-pyridyl and pyridylmethyl, pyridylcarbonylaminomethyl, pyrrolidinecarbonyl, and 2-tetrahydrofuranylmethyl.

A further particularly preferred radical Q is a radical Q-5, Q-14, Q-24, Q-25, Q-26, Q-30, Q-32, Q-34, Q-43, Q-44, Q-47, Q-49 Q-50 or Q-75, in particular a radical Q-24, Q-26, Q-30, Q-32, Q-34, Q-44 or Q-47, which is each unsubstituted or substituted by one substituent selected from the group consisting of methyl, trifluoromethyl, 2-trifluoroethyl, trifluormethylcarbonyl, cyano, methoxycarbonyl, tert.-butoxycarbanyl, carboxymethyl, ethoxy-carbonylmethyl, aminocarbonyl, N-methylaminocarbonyl, 2-trifluorethylaminocarbonyl-methyl, 2-trifluorethylaminocarbonylmethylaminocarbonyl, 1-fluoro-2-iodo-1-vinyl, —C(O)N=CHN(CH$_3$)$_2$, C(O)N=CHNHOCH$_3$, 4-chlorphenyl, 4-fluorophenyl, 4-methoxyphenyl, benzyl, 4-chlorophenylethyl, 2-, 3- and 4-pyridyl, chloropyridyl, 2-, 3- and 4-pyridylmethyl, pyrrolidinecarbonyl, tetrahydrofuranylmethyl and pyridylcarbonylaminomethyl.

Another preferred radical Q is a radical of formula wherein R is hydrogen or C$_1$-C$_2$-alkyl, halo-C$_1$-C$_2$-alkyl, halo-C$_1$-C$_2$-alkylcarbonyl, cyano, C$_1$-C$_4$-alkoxycarbonyl, C$_1$-C$_4$-alkoxycarbonylmethyl, carboxy-C$_1$-C$_2$-alkyl, aminocarbonyl, N-mono- or N,N-di-C$_1$-C$_2$-alkylaminocarbonyl, halo-C$_1$-C$_2$-alkylaminocarbonylmethyl, halo-C$_1$-C$_2$-alkylaminocarbonylmethylaminocarbonyl, halovinyl, —C(O)N=CHN(CH$_3$)$_2$, —C(O)N=CHNHOCH$_3$, unsubstituted or halogen or C$_1$-C$_2$-alkoxy-substituted phenyl, benzyl or phenylethyl, unsubstituted or halogen-substituted 2-, 3- and 4-pyridyl and pyridylmethyl, pyridylcarbonylaminomethyl, pyrrolidinecarbonyl, or 2-tetrahydrofuranylmethyl.

A suitable fused hetero-bicyclic ring system comprises, for example, a 5- or 6-membered heterocyclic, ring having from 1 to 4, preferably from 1 to 3 same or different heteroatoms selected from the group consisting of N, O and S, to which is attached an annulated ring; in addition said fused bicyclic system is further unsubstituted or substituted by one or more substituents as defined before for including the preferences given. Those rings can be saturated ring or unsaturated rings.

Examples of fused hetero-bicyclic ring systems Q are illustrated in Exhibit 3 below.

Exhibit 3

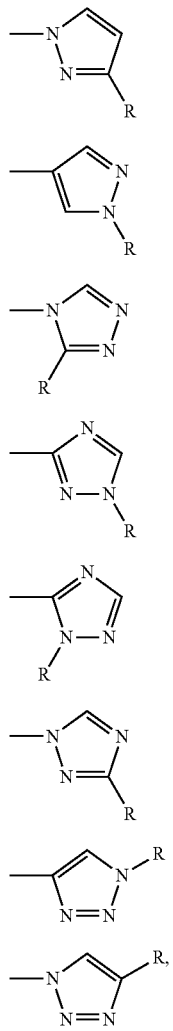
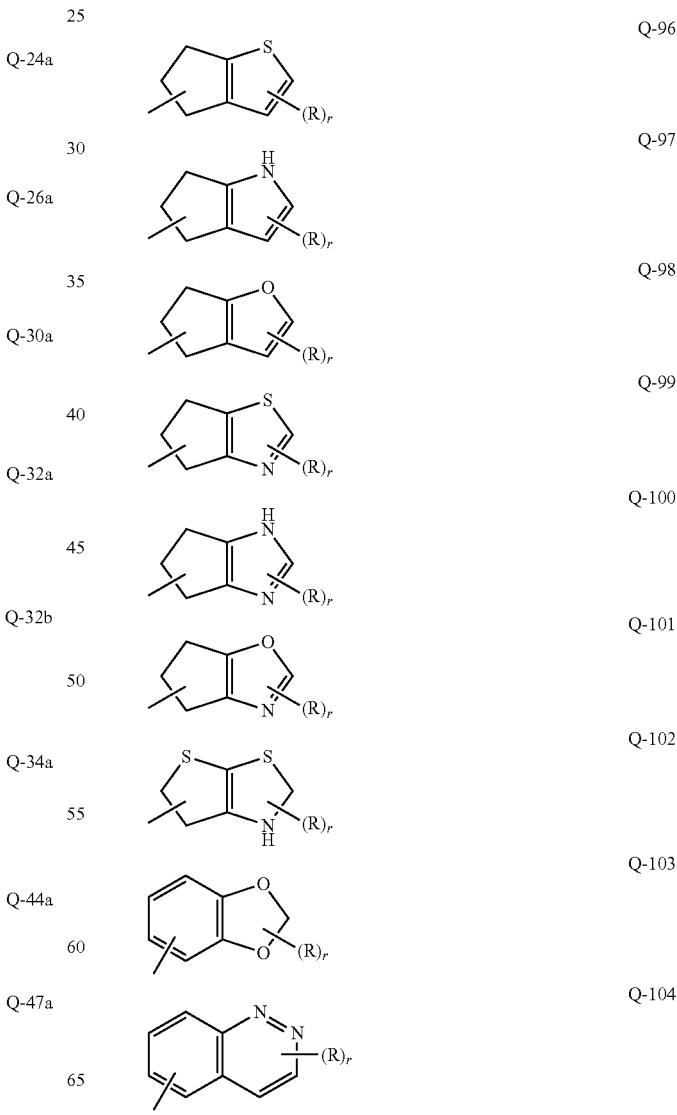

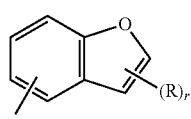 Q-105
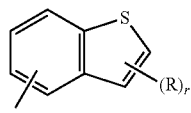 Q-106
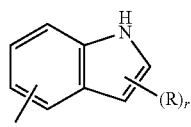 Q-107
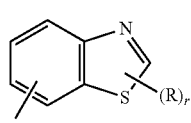 Q-108
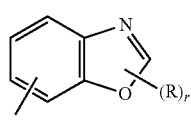 Q-109
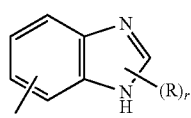 Q-110
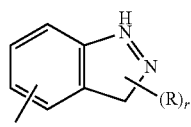 Q-111
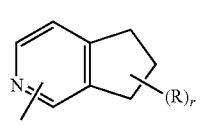 Q-112
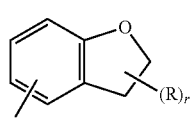 Q-113
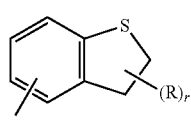 Q-114
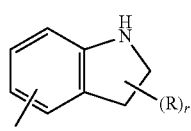 Q-115
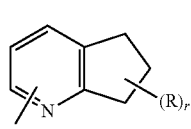 Q-116
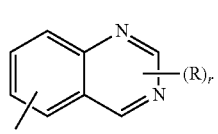 Q-117
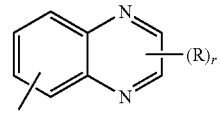 Q-118
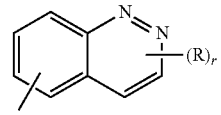 Q-119
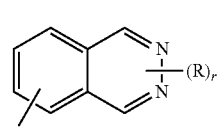 Q-120
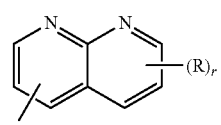 Q-121
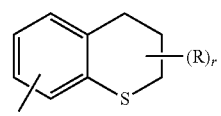 Q-122
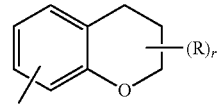 Q-123
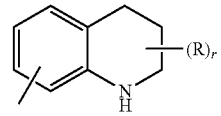 Q-124
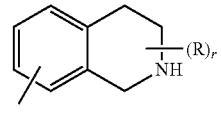 Q-125
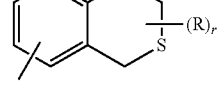 Q-126
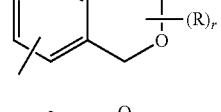 Q-127
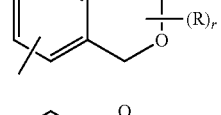 Q-128
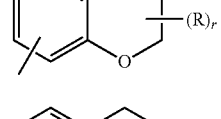 Q-129
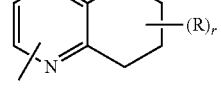 Q-130

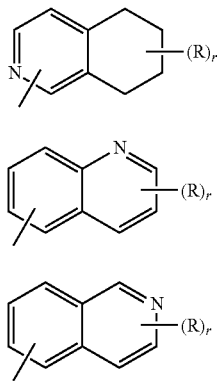

Q-131

Q-132

Q-133 wherein for $(R)_r$ each the above-given meanings and preferences apply. In the above Exhibit 3, when the attachment point on the Q group is illustrated as floating, the Q group can be attached to the remainder of the formula (I) through any available carbon or nitrogen of the Q group by replacement of a hydrogen atom. In addition, when the attachment point between $(R)_r$ and the Q group is illustrated as floating, $(R)_r$ can be attached to any available carbon atom or nitrogen atom of the Q group.

Q is even more preferred the unsubstituted radical Q-105, Q-106, Q-107, Q-108, Q-109, Q-110 or Q-111, wherein r is 0 in each case. Particularly preferred fused bicyclic structures Q are of formula

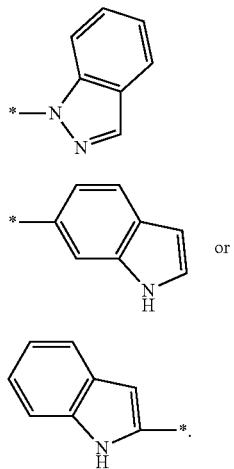

Q-111a

Q-107a or

Q-107b

A further preferred fused bicyclic structure Q is of formula

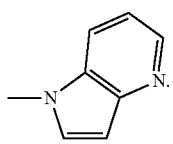

Q-134

According to a preferred embodiment of the invention there is provided a compound of formula (Ia)

including all geometric and stereoisomers, N-oxides, and salts thereof, wherein for $R_1$, $R_2$, $R_3$, Q and n each the above-given meanings and preferences apply, and m is an integer from 0 to 3.

In particular, n is an integer from 1 to 3, $R_1$ is $C_1$-$C_3$-haloalkyl, each $R_2$ and $R_3$ is independently selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN and —NO$_2$, m is an integer from 0 to 2, in particular 0, and Q is either (i) phenyl, which is unsubstituted or substituted by 1 to 3, in particular 1 or 2, same or different substituents selected from the group consisting of halogen, $C_1$-$C_2$alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$, and unsubstituted or halogen-, $C_1$-$C_2$-alkyl-, $C_1$-$C_2$haloalkyl-, $C_1$-$C_2$-alkoxy-, $C_1$-$C_2$-haloalkoxy-, —CN or —NO$_2$— substituted phenyl or phenoxy, or is (ii) a 5- or 6-membered heterocyclic ring having from 1 to 3 same or different heteroatoms selected from the group consisting of N, O and S, which is further unsubstituted or substituted by halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$ or $C_1$-$C_4$-alkoxycarbonyl, or is (iii) a fused bicyclic ring system comprising a 5- or 6-membered heterocyclic ring having from 1 to 3 same or different heteroatoms selected from the group consisting of N, O and S, to which is attached an annulated ring, and which is further unsubstituted or substituted by halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$ or $C_1$-$C_4$-alkoxycarbonyl.

A particularly preferred embodiment of the invention relates to a compound of formula (Ia) above, wherein n is an integer from 1 to 3, $R_1$ is $CF_3$, each $R_2$ is independently selected from the group consisting of halogen, $C_1$-$C_2$-haloalkyl, $C_1$-$C_2$-haloalkoxy and —CN, m is 0 and Q is either (ii) a 5- or 6-membered heteroaromatic ring selected from the group consisting of the above-given radicals Q-5, Q-6, Q-7, Q-14, Q-15, Q-16, Q-17, Q-24, Q-26, Q-30, Q-31, Q-32, Q-33, Q-34, Q-43, Q-47, Q-49, Q-50, Q-52 and Q-54, wherein r is an integer from 0 to 3 and R is independently selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$ and $C_1$-$C_4$-alkoxycarbonyl, or is (iii) a fused bicyclic ring system of formula Q-107a, Q-107b or Q-111a.

Another preferred embodiment of the invention relates to a compound of formula (Ia) above, wherein n is an integer from 1 to 3, $R_1$ is $CF_3$, each $R_2$ is independently selected from the group consisting of halogen, $C_1$-$C_2$-haloalkyl, $C_1$-$C_2$-haloalkoxy and —CN, m is 0, and is a radical Q-5, Q-14, Q-24, Q-25, Q-26, Q-30, Q-32, Q-34, Q-43, Q-44, Q-47, Q-49, Q-50, Q-52 or Q-75, which is each unsubstituted or substituted by one or more substituents selected from the group consisting of $C_1$-$C_2$-alkyl, halo-$C_1$-$C_2$-alkyl, halo-$C_1$-$C_2$-alkylcarbonyl, cyano, $C_1$-$C_4$-alkoxycarbonyl, $C_1$-$C_4$-alkoxycarbonylmethyl, carboxy-$C_1$-$C_2$-alkyl, aminocarbonyl, N-mono- or N,N-di-$C_1$-$C_2$-alkylaminocarbonyl, halo-$C_1$-$C_2$-alkylaminocarbonylmethyl, halo-$C_1$-$C_2$-alkylaminocarbanylmethylaminocarbonyl, halovinyl, —C(O)N=CHN(CH$_3$)$_2$, —C(O)N=CHNHOCH$_3$, unsubstituted or halogen or $C_1$-$C_2$-alkoxy-substituted phenyl, benzyl and phenylethyl, unsubstituted and halogen-substituted 2-, 3- and 4-pyridyl and pyridylmethyl pyridylcarbonylaminomethyl, pyrrolidinecarbonyl, and 2-tetrahydrofuranylmethyl, or Q is a radical Q-107a, Q-107b, Q-111a or Q-134.

Another preferred embodiment of the invention relates to a compound of formula (Ia) above, wherein n is an integer from 1 to 3, $R_1$ is CF$_3$, each $R_2$ is independently halogen, m is 0, and Q is a radical Q-24a, Q-26a, Q-30a, Q-32a, Q-32b, Q-34a, Q-44a or Q-47a, wherein R is hydrogen or $C_1$-$C_2$-alkyl, halo-$C_1$-$C_2$-alkyl, halo-$C_1$-$C_2$-alkylcarbonyl, cyano, $C_1$-$C_4$-alkoxycarbonyl, $C_1$-$C_4$-alkoxycarbonylmethyl, carboxy-$C_1$-$C_2$-alkyl, aminocarbonyl, N-mono- or N,N-di-$C_1$-$C_2$alkylaminocarbonyl, halo-$C_1$-$C_2$-alkylaminocarbonylmethyl, halo-$C_1$-$C_2$-alkylaminocarbonylmethylaminocarbonyl, halovinyl, —C(O)N=CHN(CH$_3$)$_2$, —C(O)N=CHNHOCH$_3$, unsubstituted or halogen or $C_1$-$C_2$-alkoxy-substituted phenyl, benzyl or phenylethyl, unsubstituted or halogen-substituted 2-, 3- and 4-pyridyl and pyridylmethyl, pyridylcarbonyl-aminomethyl, pyrrolidinecarbonyl, or 2-tetrahydrofuranylmethyl.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen containing heterocyclic rings can form N-oxides since the nitrogen requires an available lone pair for oxidations to the oxide; one skilled in the art will recognize those nitrogen containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyl dioxirane. These methods for the preparation of IV-oxides have been extensively described and reviewed in the literature.

One skilled in the art recognizes that because of the environment and under physiological conditions salts of chemical compounds are in equilibrium with their corresponding non-salt forms, salts share the biological utility of the nonsalt forms. Thus, a wide variety of salts of the compounds of formula (I) are useful for control of invertebrate pests (i.e. are veterinarily or agriculturally suitable). The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of formula (I) contains an acidic moiety such as a carboxylic acid or phenol, salts also include those formed with organic or inorganic bases such as pyridine, triethylsmine or ammonia, or amides, hydrides, hydroxides or carbonates of sodium, potassium, lithium, calcium, magnesium or barium. Accordingly, the present invention comprises compounds selected from formula (I), N-oxides and veterinary acceptable and agriculturally suitable salts thereof.

The compounds of the present invention made be prepared, for example, in analogy to the processes as outlined in WO 2007/75459 on pages 29-31. Accordingly, the compounds of formula (I) or (Ia) may be prepared, for example, by cycloaddition of a compound of formula

(II)

with a nitrile oxide derived from an oxime of formula

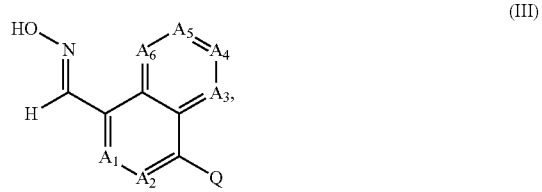

(III)

wherein $A_1$-$A_6$, $B_1$-$B_3$, $R_1$, $R_2$, Q and n each have the above-given meaning.

The reaction typically proceeds through the intermediacy of an in situ generated hydroxamyl chloride. In a typical procedure a chlorinating reagent such as sodium hypochlorite, N-chlorosuccinimide, or chloramine-T is combined with the oxime in the presence of the styrene. Depending on the conditions amine bases such as pyridine or triethylamine may be necessary. The reaction can be run in a wide variety of solvents including tetrahydrofuran, diethyl ether, methylene chloride, dioxane, and toluene with optimum temperatures ranging from room temperature to the reflux temperature of the solvent.

The compounds of formula (I) or (Ia), wherein Q is a 5-membered N-linked heterocyclic ring can also be prepared by direct displacement of an aromatic leaving group of formula

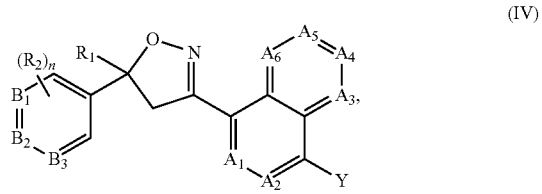

(IV)

wherein $A_1$-$A_6$, $B_1$-$B_3$, $R_1$, $R_2$ and n each have the above-given meaning and Y is halogen for example Br or F, tosylate, triflate or nitro, with a compound of the formula

Q'-H          (V).

wherein Q' is an azole heterocyclic ring, in the presence of a base. Typical azole heterocyclic rings of formula (V) include optionally substituted pyrazoles, imidazoles, triazoles and tetrazoles. Bromides can be displaced with the use of copper iodide and a palladium catalyst, sea for example Kanemasa et al., European Journal of Organic Chemistry, 2004, 695-709. For direct fluorine displacement the reaction is typically run in a polar aprotic solvent such as N,N-dimethylformamide or N,N-dimethylacetamide and in the presence of an inorganic base such as sodium or potassium carbonate.

Another process for the preparation of compounds of the formula (I) or (Ia), wherein Q is a phenyl, naphthyl or heteroaromatic ring, includes the Suzuki reaction via Pd-catalyzed cross coupling of an aromatic iodide or bromide of formula (IV) above, wherein Y is Br or J, with an aryl or heteroaryl boronic acid of formula

Q''-B(OH)$_2$ (VI).

Many catalysts are useful for this type of transformation: a typical catalyst is tetrakis-(triphenylphosphine)palladium(0). Solvents such as tetrahydrofuran, acetonitrile, diethyl ether and dioxane are suitable. The boronic adds of Formula 6 are either commercially available or can be prepared by known methods. Other methods including the Heck, Stille, Kumada and Buchwald-Hartwig coupling procedures offer many alternatives for introduction of Q heterocyclic groups. For leading references see for example Zificsak, Craig A and Hlasta, Dennis J., Tetrahedron, 2004, 60, 8991-9016, The compounds of formulae (II) and (IV) are known, for example, from WO 2006/49459 or may be prepared in analogy to the methods disclosed therein. The compounds of formula (III) may be prepared, for example, in analogy to the processes disclosed in WO 2007/75459 for the preparation of compounds of formula (3).

The compounds of the formula (I) according to the invention are notable for their broad activity spectrum and are valuable active ingredients for use in pest control. They are particularly suitable in the control of ectoparasites and to a certain extent also for controlling endoparasites on and in animals and in the hygiene field, whilst being well tolerated by warm-blooded animals.

In the context of the present invention, ectoparasites are understood to be in particular insects, acari (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericata, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys calcitrans*, horse-flies (Tabanids) with the subfamilies of Tabanidae such as *Haematopota* spp. (e.g. *Haematopota pluvialis*) and *Tabanus* spp. (e.g. *Tabanus nigrovittatus*) and Chrysopsinae such as *Chrysops* spp. (e.g. *Chrysops caecutiens*); Hippoboscids such as *Melophagus ovinus* (sheep ked); tsetse flies, such as *Glossinia* spp.; other biting insects like midges, such as Ceratopogonidae (biting midges), Simullidae (Blackflies), Psychodidae (Sandflies); but also blood-sucking insects, for example mosquitoes, such as *Anopheles* spp. *Aedes* spp and *Culex* spp., fleas, such as *Ctenocephalides felis* and *Ctenocephalides canis* (cat and dog fleas), *Xenopsylla cheopis, Pulex irritans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (Mallophaga) such as *Bovicola* (Damalinia) *ovis, Bovicola* (Damalinia) *bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes ovis* and *Psorergates* spp. and ticks. Known representatives of ticks are, for example, *Boophiius, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, horses, pigs, sheep and goats, poultry such as chickens, turkeys, guineafowls and geese, fur-bearing animals such as mink, foxes, chinchillas, rabbits and the like, as well as companion animals such as ferrets, guinea pigs, rats, hamster, cats and dogs, but also humans.

The compounds of the formula (I) according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidai effect of the active, substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds of the formula (I) can also be used against hygiene pests, especially of the order Diptera of the families Muscidae, Sarcophagidae, Anophilidae and Culicidae; the orders Orthoptera, Dictyoptera (e.g. the family Blattidae (cockroaches), such as *Blatella germanica, Blatta orientalis, Periplaneta americana*) and Hymenoptera (e.g. the families Formicidae (ants) and Vespidae (wasps).

Surprisingly, the compounds of formula (I) are also effective against ectoparasites of fishes, especially the sub-class of Copepoda (e.g. order of Siphonostomatoidae (sea lice), whilst being well tolerated by fish.

Compounds of the formula (I) also have sustainable efficacy on parasitic mites and insects of plants. In the case of spider mites of the order Acarina, they are effective against eggs, nymphs and adults of Tetranychidae (*Tetranychus* spp. and *Panonychus* spp.).

They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera.

They are similarly suitable as a soil insecticide against pests in the soil.

The compounds of formula (I) are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditylenchus, Radopholus, Rizoglyphus* etc.

Certain compounds of the formula (I) seem to be also effective against certain species of helminths.

Helminths are commercially important because they cause serious diseases in mammals and poultry, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are: *Haemonchus, Trichostrongylus, Ostertagia, Nematodirus, Cooperia, Ascaris, Bunostonum, Oesophadostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica*.

The good pesticidal activity of the compounds of formula (I) according to the invention corresponds to a mortality rate of at least 50-60% of the pests mentioned, more preferably to a mortality rate over 90%, most preferably to 95-100%. The compounds of formula (I) are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g., food additives tablets including e.g. capsules, powders including soluble powders, granules, or embeddings of the active ingredient in polymeric substances, like implants and microparticles). As with the compositions, the methods of application are selected in accordance with the intended objectives and the prevailing circumstances. The formulation, i.e. preparations containing the active ingredient of formula (I), or combinations of these active ingredients with other active ingredients, and optionally a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, carbonates, such as propylene carbonate, ketones, such as cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpalmitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application forms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholestesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™ saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers polyvinyl alcohols, polyvinylpyrrolidons and fine disperse silicium dioxide.

As polymeric agents with controlled release properties, may be applied derivatives made by e.g. polylactic acid, polylactic coglycolic acid, poly orthoester, polyethylene carbonate, poly anhydrids and starch and PVC based matrices.

The addition of penetration enhancers like ketones sulfoxides, amides, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may also applied in capsules, like hard gelatins capsules or soft capsules.

The binders for tablets and boil may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), lubricants (e.g. magnesium stearate), glidants (e.g., colloidal silicon dioxide) and disintegrants (e.g. cellulose derivatives) and acid resistant coatings, like e.g. acrylic acid esters.

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. For example, in case of a compound of formula (I) having a particular efficacy as adulticide, e.g. since the compounds of formula (I) are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I). Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers. Non-limitative examples of suitable insecticides and acaricides are mentioned in WO 2009/071500, compounds Nos. 1-284 on pages 18-21. Non-limitative examples of suitable anthelminthics are mentioned in WO 2009/071500, compounds (A1)-(A31) on page 21. Non-limitative examples of suitable repellents and detachers are mentioned in WO 2009/071500, compounds (R1)-(R3) on page 21 and 22. Non-limitative examples of suitable synergists are mentioned in WO 2009/071500, compounds (S1)-(S3) on page 22. The said partners in the mixture are best known to specialists in this field. Most are described in various editions of the Pesticide Manual, The British Crop Protection Council, London, and others in the various editions of The Merck Index, Merck & Inc., Rahway, N.J., USA or in patent literature. A list of suitable partners including a reference is disclosed in WO 2005/058802 on pages 16-21, No. (I) to (CLXXXIII).

As a consequence of the above details, a further aspect of the present invention relates to a combination preparation for the control of parasites on warm-blooded animals, characterised in that it contains, in addition to a compound of formula (I), at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of one or more active ingredients of formula (I), 99.9 to 1% by weight, especially 99.8 to 5% by weight of a solid or liquid admixture, including 0 to 25% by weight, especially 0.1 to 25% by weight of a surfactant. Application of the compositions according to the invention to the animals to be treated may take place topically, perorally, parenterally or subcutaneously, the composition being present, for example, in the form of solutions, emulsions, suspensions, (drenches), powders, tablets, boli, capsules, collars, eartags and pour-on formulations.

Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to 1 ml per kg, preferably about 0.1 ml per kg, with a to volume from 0.1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol of synthetic triglycerides.

The oily solutions include e.g. vegetable, oils such as olive oil, groundnut oil, sesame oil, pine oil, linseed oil or castor oil. The vegetable oils may also be present in epoxidised form.

Paraffins and silicone oils may also be used.

A pour-on or spot-on formulation generally contains 1 to 98.9% by weight of a compound of formula (I), 0.1 to 80% by weight of dispersing agent and 1 to 98.9% by weight of solvent. The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including it domestic animals or pets, and is greatly favoured by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates. Such compositions may also contain further additives, such as stabilisers, anti-foaming agents, viscosity regulators, binding agents or tackifiers, a well as other active ingredients, in order to achieve special effects.

Insecticidal and acaricidal compositions of this type, which are used by the end user, similarly form a constituent of the present invention.

In each of the processes according to the invention for pest control or in each of the pest control compositions according to the invention, the active ingredients of formula (I) can be used in all of their steric configurations or in mixtures thereof.

The invention also includes a method of prophylactically protecting animals, especially productive livestock, domestic animals and pets, against parasitic, helminths, which is characterised in that the active ingredients of formula (I) or the active ingredient formulations prepared therefrom are administered to the animals as an additive to the feed, or to the drinks or also in solid or liquid form, orally or by injection or parenterally. The invention also includes the compounds of formula (I) according to the invention for usage in one of the said processes.

The following examples serve merely to illustrate the invention without restricting it, the term active ingredient representing any substance as described in the preparation examples, in particular, preferred formulations are made up as follows:

(%=percent by weight)

FORMULATION EXAMPLES

1. Granulate

|   |   | a) | b) |
|---|---|---|---|
| (i) | active ingredient | 5% | 10% |
|   | kaolin | 94% | — |
|   | highly dispersed silicic acid | 1% | — |
|   | attapulgite | — | 90% |

The active ingredient is dissolved in methylene chloride, sprayed onto the carrier and the solvent subsequently concentrated by evaporation under vacuum. Granulates of this kind can be mixed with the animal feed.

| (ii) | active ingredient | 3% |
|---|---|---|
|   | polyethylene glycol (mw 200) | 3% |
|   | kaolin | 94% |

(mw = molecular weight)

The finely ground active ingredient is evenly applied in a mixer to the kaolin which has been moistened with polyethylene glycol, in this way, dust-free coated granules are obtained, 2. Tablets or Boli

| I | active ingredient | 33.00% |
|---|---|---|
|   | methylcellulose | 0.80% |
|   | silicic acid, highly dispersed | 0.80% |
|   | corn starch | 8.40% |
| II | lactose, cryst. | 22.50% |
|   | corn starch | 17.00% |
|   | microcryst. cellulose | 16.50% |
|   | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

3. Injectables

A. Oily Vehicle (Slow Release))

| (i) | active ingredient | 0.1-1.0 g |
|---|---|---|
|   | groundnut oil | ad 100 ml |
| (ii) | active ingredient | 0.1-1.0 g |
|   | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 μm.

B Water-Miscible Solvent (Average Rate of Release)

| (i) | active ingredient | 0.1-1.0 g |
|---|---|---|
|   | 4-hydroxymethyl-1,3-dioxolane (glycerol formal) | 40 g |
|   | 1,2-propanediol | ad 100 ml |
| (ii) | active ingredient | 0.1-1.0 g |
|   | glycerol dimethyl ketal | 40 g |
|   | 1,2-propanediol | ad 100 ml |

Preparation: The active ingredient is dissolved in part of the solvent whilst stirring, made up to the desired volume and sterile-filtered through a suitable membrane filter with a pore size of 0.22 μm.

C. Aqueous Solubilisate (Rapid Release)

| (i) | active ingredient | 0.1-1.0 g |
|---|---|---|
|   | polyethoxylated castor oil (40 ethylene oxide units) | 10 g |
|   | 1,2-propanediol | 20 g |
|   | benzyl alcohol | 1 g |
|   | aqua ad inject. | ad 100 ml |
| (ii) | active ingredient | 0.1-1.0 g |
|   | polyethoxylated sorbitan monooleate (20 ethylene oxide units) | 8 g |
|   | 4-hydroxymethyl-1,3-dioxolane (glycerol formal) | 20 g |
|   | benzyl alcohol | 1 g |
|   | aqua ad inject. | ad 100 ml |

Preparation: The active ingredient is dissolved in the solvents and the surfactant and made up with water to the desired volume. Sterile filtration through an appropriate membrane filter of 0.22 μm pore size.

4. Pour On

| (i) | active ingredient | 5 g |
|---|---|---|
|   | isopropyl myristate | 10 g |
|   | isopropanol | ad 100 ml |
| (ii) | active ingredient | 2 g |
|   | hexyl laurate | 5 g |
|   | medium-chained triglyceride | 15 g |
|   | ethanol | ad 100 ml |
| (iii) | active ingredient | 2 g |
|   | oleyl oleate | 5 g |
|   | N-methyl-pyrrolidone | 40 g |
|   | isopropanol | ad 100 ml |

5. Spot On

| (i) | active ingredient | 10-15 g |
|---|---|---|
|   | diethyleneglycol monoethylether | ad 100 ml |
| (ii) | active ingredient | 10-15 g |
|   | octyl palmitate | 10 g |
|   | isopropanol | ad 100 ml |
| (iii) | active ingredient | 10-15 g |
|   | isopropanol | 20 g |
|   | benzyl alcohol | ad 100 ml |

6. Spray On

| (i) | active ingredient | 1 g |
|---|---|---|
|   | isopropanol | 40 g |
|   | propylene carbonate | ad 100 ml |
| (ii) | active ingredient | 1 g |
|   | propylene glycol | 10 g |
|   | isopropanol | ad 100 ml |

The aqueous systems may also preferably be used for oral and/or intraruminal application. The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula (I) and do not have a harmful effect on the host animal to be treated, as well as mineral salts or vitamins, may also be added to the described compositions.

The following examples serve to illustrate the invention. They do not limit the invention. The letter 'h' stands for hour. The starting materials are known and partially commercially available or may be produced in analogy to methods known per se.

Analysis of the purified samples is in each case done using a Waters Autopurification (HPLC/MS) system with a reversed phase column (Daisogel SP-120-ODS-AP 5 μm, 150×3 mm) from Bischoff, Leonberg, Germany. The samples are characterized by m/z and retention time. The above-given retention times relate in each ease to the use of a solvent system comprising two different solvents, solvent A: $H_2O$+ 0.01% HCOOH, and solvent B: $CH_3CN$+0.01% HCOOH. Said two solvents A and B are employed at a flow rate of 2.00 ml/min with a time-dependent gradient as given in the Table:

| Time [min] | A [%] | B [%] |
|---|---|---|
| 0.5 | 10 | 90 |
| 1.0 | 26 | 74 |
| 1.5 | 40 | 60 |
| 2.0 | 53 | 47 |
| 2.5 | 64 | 36 |
| 3.0 | 74 | 26 |
| 3.5 | 81 | 19 |
| 4.0 | 87 | 13 |
| 4.25 | 90 | 10 |
| 4.5 | 92 | 8 |
| 4.75 | 93 | 7 |
| 5.0 | 94 | 6 |
| 5.5 | 95 | 5 |
| 6.5 | 95 | 5 |

Example 1

Preparation of 1-{4-[5-(3,5-dichloro-phenyl)-5-trifluoromethyl-4,5-dihydro-isoxazol-3-yl]-naphthalen-1-yl}-1H-[1,2,4]triazole (compound 1.1, Table 1)

Step 3,3,3-Trifluoropropene (3.2 g), potassium carbonate (4.6 g) and bis-(triphenylphosphine)-palladium chloride (0.2 g) are added to a solution of 3,5-dichlorophenylboronic acid in THF (20 ml) under nitrogen. After 3 hours at reflux, the reaction is quenched with ethyl acetate (50 ml) and water (50 ml). The organic phase is then extracted with water and with a saturated aqueous solution of NaCl, dried over $Na_2SO_4$ and concentrated in vacuo. The crude product is purified on silica gel (35×45 mm) using heptane (150 ml) as eluant to yield 1,3-dichloro-5-(1-trifluoromethyl)vinyl)-benzene (2.7 g), as a colorless oil. MS (HPLC/MS): no ionisation. Retention time: 5.10 min, Step B: $SnCl_4$ (13 ml, 1M solution in dichloromethane) is added to a solution of dichlormethyl-methylether in dichloromethane (6 ml) at 0° C. After 1 hour at 0° C., a solution of 1-fluoro-naphtalene (1.46 g) in dichloromethane (4 ml) is added over 10 minutes. The reaction is stirred overnight at room temperature and then quenched with cold water (30 ml). The organic phase is separated and the aqueous phase is extracted 3 times with dichloromethane. The combined organic phases are dried over $Na_2SO_4$ and concentrated in vacuo to yield 4-fluoro-naphthalene-1-carbaldehyde (1.73 g, dark brown crystals). The crude product obtained is used without further purification, MS (HPLC/MS): no ionisation. Retention time: 3.88 min.

Step C: 1,2,4-triazole (248 mg) is added to a solution of 4-fluoro-naphthalene-1-carbaldehyde (522 mg) and potassium carbonate (4 mg) in DMF (4 ml): After 3 hours a room temperature, the reaction is quenched with water (40 ml) and ethyl acetate (50 ml). The organic phase is separated and the aqueous phase is extracted two times with ethyl acetate. The organic phases are combined, extracted with water and with a saturated aqueous solution of NaCl, dried over $Na_2SO_4$ and concentrated in vacuo. The crude product is purified on a semi-preparative HPLC to yield 4-[1,2,4]triazol-1-yl-naphthalene-1-carbaldehyde (460 mg) as beige crystals. MS (HPLC/MS): 224 ($MH^+$). Retention time: 2.97 min.

Step D: Sodium acetate (262 mg) is added to a solution of hydroxylamine hydrochloride (193 mg) and 4-[1,2,4]triazol-1-yl-naphthalene-1-carbaldehyde (455 mg) in THF (16 ml), water (2 ml) and DMSO (2 ml). After 5 hours at room temperature, the reaction is quenched with water and ethyl acetate. The organic phase is separated and the water phase is extracted with ethyl acetate. The combined organic phases are extracted with water and with a saturated aqueous solution of NaCl, dried over $Na_2SO_4$ and concentrated in vacuo to yield 4-[1,2,4]triazol-1-yl-naphthalene-1-carbaldehyde oxime. The crude product obtained (390 mg, beige crystals) is used without further purification. MS (HPLC/MS): 239 ($MH^+$). Retention time 2.76 min.

Step E: N-chlorosuccinimid (220 mg) is added to a solution of 4-[1,2,4]triazol-1-yl-naphthalene-1-carbaldehyde oxime (390 mg) in DMF (5 ml). After 45 minutes at 40° C., the reaction is cold down to 0° C., and 1,3-dichloro-5-(1-trifluoromethyl-vinyl)-benzene (394 mg, Example 1, step A) and triethylamine (0.25 ml) are added. The reaction is then further reacted at room temperature for 3 hours. Water is added (50 ml) and the reaction mixture is extracted two times with ethyl acetate. The organic phase is extracted, with a saturated aqueous solution of NaCl, dried over $Na_2SO_4$ and concentrated in vacuo. The crude product is purified on a semi-preparative HPLC: to yield 1-{4-[5-(3,5-dichloro-phenyl)-5-trifluoromethyl-4,5-dihydro-isoxazol-3-yl]-naphthalen-1-yl}-1H-[1,2,4]triazole (500 mg) as beige crystals. MS (HPLC/MS): 477 ($MH^+$). Retention time: 5.20 min.

Example 2

Preparation of 5-(3,5-dichloro-phenyl)-3-[4-(1H-pyrazol-4-yl)-naphthalen-1-yl]-5-trifluoromethyl-4,5-dihydro-isoxazole (compound 1.17, Table 1)

Step A: A solution of benzoyl peroxide (87 mg) in trifluorotoluene (40 ml) is refluxed for 30 min under nitrogen. The reaction mixture is cooled to 78° C. and 1-bromo-4-methyl-naphthalene (1.6 ml) and N-bromasuccinimide (2.0 g) are added. The reaction is stirred for 1.5 hours at 78° C. and filtered. The filtrate is concentrated in vacuo and the residue crystallized in heptane to yield 1-bromo-4-bromomethyl-naphthalene. The crude product is used in the next step without further purification.

Step B: Sodium bicarbonate (1.4 g) is added to a solution of crude 1-bromo-4-bromomethyl-naphthalene (2.5 g) in DMSO (25 ml). The reaction is stirred for 3 h at 95° C. and cooled down to room temperature. Water is added and the mixture is extracted with ethyl acetate. The organic phase is dried over $MgSO_4$ and concentrated in vacuo. The crude product is purified on a semi-preparative HPLC to yield 4-bromo-naphthalene-1-carbaldehyde as colorless crystals.

Step C: Hydroxylamine (50% aqueous, 0.37 ml) is added to a solution of 4-bromo-naphthalene-1-carbaldehyde (0.7 g) in methanol (6 ml). After 16 hours at room temperature the reaction is concentrated in vacuo to yield crude 4-bromo-naphthalene-1-carbaldehyde oxime, which is used in the next step without further purification.

Step D: N-chlorosuccinimid (134 mg) is added to a solution of crude 4-bromo-naphthalene-1-carbaldehyde oxime (250 mg) in DMF (3 ml). After 1 hour at 40° C., the reaction is cooled down to 0° C. and 1,3-dichloro-5-(1-trifluoromethyl-vinyl)-benzene (240 mg) and triethylamine (0.15 ml) are added. The reaction is further reacted at room temperature for 16 hours. Water is added and the reaction mixture is extracted with ethyl acetate. The organic phase is washed with a saturated aqueous solution of NaCl, dried over $MgSO_4$ and concentrated in vacuo. The crude product is purified on a semi-preparative HPLC to yield 3-(4-bromo-naphthalen-1-yl)-5-(3,5-dichloro-phenyl)-5-trifluoromethyl-4,5-dihydro-isoxazole as colorless crystals: m.p. 127-130° C.

Step E: 1-Tert-butoxycarbonyl-4-1H-pyrazoleboronic acid pinacol ester (126 mg), Tris(dibenzylideneacetone)dipalladium(0) $[Pd_2(dba)_3$ (7 mg)], $K_3PO_4$ (185 mg) and 2-dicyclohexylphosphinno-2',6'-dimethoxybiphenyl (12 mg) are added to a solution of 3-(4-bromo-naphthalen-1-yl)-5-(3,5-dichloro-phenyl)-5-trifluoromethyl-4,5-dihydro-isoxazole (140 mg) in dry toluene (2.4 ml). After 16 hours at 75° C. the reaction is cooled down to room temperature and filtrated. The filtrate is concentrated in vacuo. The crude product is purified on a semi-preparative HPLC to yield 4-{4-[5-(3,5-dichloro-phenyl)-5-trifluoromethyl-4,5-dihydro-isoxazol-3-yl]-naphthalen-1-yl}-pyrazole-1-carboxylic acid tert-butyl ester (compound 1.10, Table 1) as a colorless oil.

Step F: Trifluoroacetic acid anhydride (0.18 ml) is added to a solution of 4-{4-[5-(3,5-dichloro-phenyl)-5-trifluoromethyl-4,5-dihydro-isoxazol-3-yl]-naphthalen-1-yl}-pyrazole-1-carboxylic acid tert-butyl ester (135 mg) in dichloromethane (1 ml). After 1 hour at room temperature an aqueous solution of sodium hydroxide (30%) is added. The aqueous phase is extracted with dichloromethane and the combined organic phases are dried over $MgSO_4$ and concentrated in vacuo. The crude product is purified on a semi-preparative HPLC to yield 5-(3,5-dichloro-phenyl)-3-[4-(1H-pyrazol-4-yl)-naphthalen-1-yl]-5-trifluoromethyl-4,5-dihydro-isoxazole as a colorless solid: m.p. 117-120° C. (compound 1.17, table 1).

Example 3

Preparation of 5-(3,5-dichloro-phenyl)-3-{4-[1-(2,2,2-trifluoro-ethyl)-1H-pyrazol-4-yl]-naphthalen-1-yl}-5-trifluoromethyl-4,5-dihydro-isoxazole (compound 1.18, Table 1)

Sodium hydride (2 mg) is added to a solution of 5-(3,5-dichloro-phenyl)-3-[4-(1H-pyrazol-4-yl)-naphthalen-1-yl]-5-trifluoromethyl-4,5-dihydro-isoxazole (3 mg, Example 2) in DMF (0.4 ml) at 0° C. After 1 hour at room temperature 2-iodo-1,1,1,-trifluoroethane (16 mg) is added and the reaction mixture is further stirred for 16 hours at room temperature. Water is added and the reaction mixture is extracted with ethyl acetate. The organic phase is washed with a saturated aqueous solution of NaCl, dried over $MgSO_4$ and concentrated in vacuo. The crude product is purified on a semi-preparative HPLC to yield 5-(3,5-dichloro-phenyl)-3-{4-[1-(2,2,2-trifluoro-ethyl)-1H-pyrazol-4-yl]-naphthalen-1-yl}-5-trifluoromethyl-4,5-dihydro-isoxazole (compound 1.18, Table 1) as a colorless wax.

Example 4

Preparation of 2-(4-{4-[5-(3,5-dichloro-phenyl)-5-trifluoromethyl-4,5-dihydro-isoxazol-3-yl]-naphthalen-1-yl}-[1,2,3]triazol-1-ylmethyl)-pyridine (compound 1.27, Table 1)

Step A: Trimethylsilylacetylene (0.42 ml), triethylamine (0.42 ml), CuI (38 mg) and $Pd(PPh_3)_2Cl_2$ (98 mg) are added to a solution of 3-(4-bromo-naphthalen-1-yl)-5-(3,5-dichloro-phenyl)-5-trifluoromethyl-4,5-dihydro-isoxazole (1.0 g, example 2 step D) in DMF (10 ml). The reaction is stirred for 16 hours at room temperature. Water is added and the reaction mixture is extracted with ethyl acetate. The organic phase is washed with a saturated aqueous solution of NaCl, dried over $MgSO_4$ and concentrated in vacuo. The crude 5-(3,5-dichloro-phenyl)-5-trifluoromethyl-3-(4-trimethylsilanylethynyl-naphthalen-1-yl)-4,5-dihydro-isoxazole is used in the next step without further purification.

Step B: A solution of tetrabutylammonium chloride (1 M in THF, 2.25 ml) is slowly added to a solution of crude 5-(3,5-dichloro-phenyl)-5-trifluoromethyl-3-(4-trimethylsilanyl-ethynyl-naphthalen-1-yl)-4,5-dihydro-isoxazole (step A) in THF (25 ml) at 5° C. After 3 hours at 5° C. a saturated solution of ammonium chloride and ethyl acetate are added. The organic phase is washed with a saturated aqueous solution of NaCl, dried over $MgSO_4$ and concentrated in vacuo. The crude product is purified on a semi-preparative HPLC to yield 5-(3,5-dichloro-phenyl)-3-(4-ethynyl-naphthalen-1-yl)-5-trifluoromethyl-4,5-dihydro-isoxazole as a brown solid.

Step C: CuI (88 mg) is added to a solution of 2-azidomethyl-pyrimidine (62 mg), N,N-diisopropylethylamine (DIPEA, 2.0 ml) and 5-(3,5-dichloro-phenyl)-3-(4-ethynyl-naphthalen-1-yl)-5-trifluoromethyl-4,5-dihydro-isoxazole (100 mg) in DMF (1.0 ml). After 16 hours at room temperature, the reaction is quenched with a saturated solution of $NaHCO_3$ and extracted with dichloromethane. The combined organic phases are dried over $MgSO_4$ and concentrated in vacuo. The crude product is purified on a semi-preparative HPLC to yield 2-(4-{4-[5-(3,5-dichloro-phenyl)-5-trifluoromethyl-4,5-dihydro-isoxazol-3-yl]-naphthalen-1-yl}-[1,2,3]triazol-1-ylmethyl)-pyridine as a beige foam. (compound 1.27, Table 1).

Example 5

Preparation of N-(1-{4-[5-(3,5-dichloro-phenyl)-5-trifluoromethyl-4,5-dihydro-isoxazol-3-yl]-naphthalen-1-yl}-1H-[1,2,3]triazol-4-ylmethyl)-isonicotinamide (compound 1.61, Table 1)

Step A: Sodium acetate (4.8 g) is added to a solution of hydroxylamine hydrochloride (2.9 g) and 4-fluoro-naphthalene-1-carbaldehyde (8.1 g, example 1 step B) in THF (40 ml) and water (10 ml). After 3 hours at room temperature, the reaction is quenched with water and ethyl acetate. The organic, phase is separated and the water phase is extracted with ethyl acetate. The combined organic phases are washed with water and with a saturated aqueous solution of NaCl, dried over $Mg_2SO_4$ and concentrated in vacuo to yield 4-fluoro-naphthalene-1-carbaldehyde oxime. The crude product obtained is used without further purification.

Step B: N-chlorosuccinimid (4.7 g) is added to a solution of 4-fluoro-naphthalene-1-carbaldehyde oxime (6.6 g, example 5 step A) in DMF (50 ml). After 45 minutes at 40° C., the reaction is cooled down to 0° C. and 1,3-dichloro-5-(1-trifluoromethyl-vinyl)-benzene, (8.4 g, example 1 step A) and triethylamine (5.4 ml) are added. The reaction is then further reacted at room temperature for 3 hours. Water is added (50 ml) and the reaction mixture is extracted with ethyl acetate. The organic phase is washed with a saturated aqueous solution of NaCl, dried over $MgSO_4$ and concentrated in vacuo. The crude product is dissolved in dichloromethane and filtered over a pad of silica gel to yield 5-(3,5-dichloro-phenyl)-3-(4-fluoro-naphthalen-1-yl)-5-trifluoromethyl-4,5-dihydro-isoxazole as a beige solid.

Step C: Sodium azide (3.3 g) is added to a solution of 5-(3,5-dichloro-phenyl)-3-(4-fluoro-naphthalen-1-yl)-5-trifluoromethyl-4,5-dihydro-isoxazole (10.7 g) in DMF (50 ml). After 20 hours at 80° C. another portion of sodium azide is added (3.3 g) and the reaction mixture is stirred for 20 hours at 80° C. The solution is cooled to room temperature and the volume concentrated to 10 ml in vacuo. Water and ethyl acetate are added and the precipitate is collected after filtration to yield 3-(4-azido-naphthalen-1-yl)-5-(3,5-dichloro-phenyl)-5-trifluoromethyl-4,5-dihydro-isoxazole as a beige solid: 183-185° C.

Step D: CuI (211 mg) is added to a solution of 3-(4-azido-naphthalen-1-yl)-5-(3,5-dichloro-phenyl)-5-trifluoromethyl-4,5-dihydro-isoxazole (500 mg), DIPEA (3.3 ml) and N-prop-2-ynyl-isonicotinamide (180 mg) in DMF (2.0 ml). After 5 hours at room temperature, the reaction is quenched with a saturated solution of $NaHCO_3$ and extracted with dichloromethane. The combined organic phases are dried over $Na_2SO_4$ and concentrated in mow. The crude product is purified on a semi-preparative HPLC to yield N-(1-{4-[5-(3,5-dichloro-phenyl)-5-trifluoromethyl-4,5-dihydro-isoxazol-3-yl]-naphthalen-1-yl}-1H-[1,2,3]triazol-4-ylmethyl)-isonicotinamide as a colorless oil.

Table 1 provides further compounds of formula

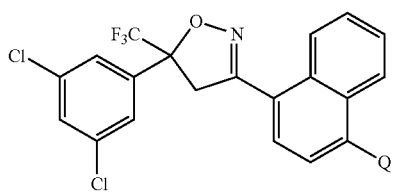

wherein the meaning of Q is given Table 1. The substances are prepared analogously to the above-described methods. The following physical data are obtained according to the above-described HPLC/MS characterization process. The values of the melting point are indicated in ° C.

TABLE 1

| Compound No. | Q | $EM_{calcd}$ | m/z | $R_t$ [min] | M.p. [° C.] |
|---|---|---|---|---|---|
| 1.1 | *—N(triazole) | 476 | 477 | 5.20 | 190-196 |
| 1.2 | *—N(pyrazole) | 475 | 476 | 5.61 | 140-145 |
| 1.3 | *—N(pyrazole-CF$_3$) | 543 | 544 | 5.99 | wax |
| 1.4 | *—N(methylpyrazole-CF$_3$) | 557 | 558 | 6.10 | wax |
| 1.5 | *—N(imidazole) | 475 | 476 | 4.10 | 198-199 |
| 1.6 | *—N(tetrazole) | 476 | 477 | 4.72 | 194-197 |
| 1.7 | *—N(indazole) | 525 | 526 | 5.52 and 5.83 | foam |
| 1.8 | *—N(triazole) | 476 | 477 | 5.29 | wax |
| 1.9 | *—phenyl-CF$_3$ | 553 | — | 6.26 | 65-68 |
| 1.10 | *—pyrazole-Boc | 575 | 576 | 5.59 | 118-121 |
| 1.11 | *—N,N-dimethylpyrazole | 517 | 518 | 5.36 | 70-74 |
| 1.12 | *—N-methylpyrazole | 489 | 490 | 7.49 | 170-173 |

TABLE 1-continued

| Compound No. | Q | EM_caled | m/z | R_t [min] | M.p. [° C.] |
|---|---|---|---|---|---|
| 1.13 | 6-indolyl (1H-indol-6-yl) | 524 | 525 | 5.70 | 199-202 |
| 1.14 | 4-pyridyl | 486 | 487 | 8.45 | 189-192 |
| 1.15 | 3-pyridyl | 486 | 487 | 8.11 | 127-130 |
| 1.16 | 1H-indol-2-yl | 524 | 525 | 8.10 | — |
| 1.17 | 1H-pyrazol-4-yl | 475 | 476 | 7.15 | 117-120 |
| 1.18 | 1-(2,2,2-trifluoroethyl)-1H-pyrazol-4-yl | 557 | 558 | 5.15 | wax |
| 1.19 | 1-methyl-3-(trifluoromethyl)-1H-pyrazol-5-yl | 557 | — | 5.51 | 195-198 |
| 1.20 | 1-(ethoxycarbonylmethyl)-1H-pyrazol-4-yl | 561 | 562 | 4.96 | — |
| 1.21 | 1-[(2,2,2-trifluoroethylcarbamoyl)methyl]-1H-indol-6-yl | 663 | 664 | 5.23 | — |
| 1.22 | 1-(carboxymethyl)-1H-pyrazol-4-yl | 533 | 534 | 4.38 | — |
| 1.23 | 1-[(2,2,2-trifluoroethylcarbamoyl)methyl]-1H-pyrazol-4-yl | 614 | 615 | 4.61 | — |
| 1.24 | 1-[(2,2,2-trifluoroethylcarbamoyl)methyl]-1H-1,2,3-triazol-4-yl | 615 | 616 | 4.46 | 185-188 |
| 1.25 | 1-benzyl-1H-1,2,3-triazol-4-yl | 566 | 567 | 5.10 | — |
| 1.26 | 1-(ethoxycarbonylmethyl)-1H-1,2,3-triazol-4-yl | 562 | 563 | 4.87 | — |
| 1.27 | 1-(pyridin-2-ylmethyl)-1H-1,2,3-triazol-4-yl | 567 | 568 | 4.66 | foam |

TABLE 1-continued

| Compound No. | Q | EM_calcd | m/z | R_t [min] | M.p. [°C.] |
|---|---|---|---|---|---|
| 1.28 | 4-pyridylmethyl-triazole | 567 | 568 | 4.08 | foam |
| 1.29 | 3-pyridylmethyl-triazole | 567 | 568 | 4.24 | foam |
| 1.30 | 2-pyridylmethyl-pyrazole | 566 | 567 | 5.18 | oil |
| 1.31 | 6-chloro-2-pyridyl-triazole | 587 | — | 6.79 | — |
| 1.32 | 1H-triazole | 476 | 477 | 5.11 | oil |
| 1.33 | 1H-triazole | 476 | 477 | 4.92 | foam |
| 1.34 | tetrahydrofurfuryl-triazole | 560 | 561 | 5.01 | 153-156 |
| 1.35 | 5-pyrimidinylmethyl-triazole | 568 | 569 | 4.34 | oil |
| 1.36 | 4-pyridyl-triazole | 553 | 554 | 4.83 | foam |
| 1.37 | triazole-carboxamide-CH2CF3 | 601 | 602 | 4.82 | wax |
| 1.38 | 2-pyridylmethyl-triazole | 567 | 568 | 5.24 | wax |
| 1.39 | 4-chlorophenethyl-triazole | 614 | 615 | 5.41 | foam |
| 1.40 | 4-fluorophenyl-triazole | 570 | 571 | 5.35 | 193-196 |
| 1.41 | CF3-oxazoline | 546 | 547 | 5.28 | oil |
| 1.42 | 4-chlorophenyl-triazole | 586 | 587 | 5.67 | 204-207 |
| 1.43 | 4-methoxyphenyl-triazole | 582 | 583 | 5.35 | 220-223 |

TABLE 1-continued

| Compound No. | Q | EM_calcd | m/z | R_t [min] | M.p. [°C.] |
|---|---|---|---|---|---|
| 1.44 | oxazoline-CF3 | 546 | 547 | 5.35 | foam |
| 1.45 | triazole-CF=CHI (isomer) | 646 | 647 | 5.64 | wax |
| 1.46 | triazole-CF=CHI (isomer) | 646 | 647 | 6.26 | wax |
| 1.47 | triazole-CH2-C(O)NH-CH2CF3 | 615 | 616 | 4.47 | oil |
| 1.48 | triazole-CH2-tetrahydrofuran | 560 | 561 | 4.93 | foam |
| 1.49 | triazole-CH2-tetrahydrofuran | 560 | 561 | 4.60 | wax |
| 1.50 | triazole-CH2-pyridine | 567 | 568 | 4.24 | wax |
| 1.51 | triazole-(3-Cl-phenyl) | 586 | 587 | 5.73 | 181-184 |
| 1.52 | triazole-(2-Cl-phenyl) | 586 | 587 | 5.42 | 232-235 |
| 1.53 | triazole-(3-OMe-phenyl) | 582 | 583 | 5.42 | 163-166 |
| 1.54 | triazole-(2-OMe-phenyl) | 582 | 583 | 5.33 | 244-247 |
| 1.55 | pyrazole-CH2-pyridine | 566 | 567 | 4.51 | oil |
| 1.56 | pyrazole-CH2-tetrahydrofuran | 559 | 560 | 4.53 | oil |
| 1.57 | triazole-CH2-pyrimidine | 568 | 569 | 5.57 | 206-209 |

TABLE 1-continued

| Compound No. | Q | EM$_{calcd}$ | m/z | R$_t$ [min] | M.p. [° C.] |
|---|---|---|---|---|---|
| 1.58 | 2-pyridyl-triazole | 553 | 554 | 4.94 | foam |
| 1.59 | 3-pyridyl-triazole | 553 | 554 | 4.83 | 235-237 |
| 1.60 | CF$_3$CH$_2$NHC(O)-triazole | 601 | 602 | 4.60 | oil |
| 1.61 | 4-pyridyl-C(O)NHCH$_2$-triazole | 610 | 611 | 4.05 | oil |
| 1.62 | MeO$_2$C-triazole | 534 | 535 | 4.69 | foam |
| 1.63 | Me$_2$NC(O)-triazole | 547 | 548 | 4.40 | foam |
| 1.64 | pyrrolo[2,3-b]pyridine | 525 | 526 | 5.00 | wax |
| 1.65 | CF$_3$C(O)-pyrazole | 570 | 571 | 5.78 | wax |
| 1.66 | NC-triazole | 501 | — | 5.33 | 206-208 |
| 1.67 | MeO$_2$C-triazole | 534 | — | 4.57 | foam |
| 1.68 | HO$_2$C-triazole | 520 | 521 | 4.67 | 161-164 |
| 1.69 | H$_2$NC(O)-triazole | 519 | 520 | 4.18 | 279-280 |
| 1.70 | MeNHC(O)-triazole | 533 | 534 | 4.29 | 174-176 |
| 1.71 | Me$_2$N-CH=N-C(O)-triazole | 574 | 575 | 3.95 | 228-229 |
| 1.72 | MeO-NH-CH=N-C(O)-triazole | 576 | 577 | 4.89 | 179-181 |

TABLE 1-continued

| Compound No. | Q | $EM_{calcd}$ | m/z | $R_t$ [min] | M.p. [° C.] |
|---|---|---|---|---|---|
| 1.73 | *-triazole-C(O)-NH-CH2-C(O)-NH-CH2-CF3 | 658 | 659 | 4.27 | wax |
| 1.74 | *-triazole-C(O)-pyrrolidine | 573 | 574 | 4.61 | wax |

Biological Examples

1. Activity In Vivo Against *Ctenocephalides felis* (Cat Flea).

A mixed adult population of fleas is placed in a suitably formatted 96-well plate allowing fleas to access and feed on treated blood via an artificial feeding system. Fleas are fed on treated blood for 24 hours, after which the compound's effect is recorded. Insecticidal activity is determined on the basis of the number of dead fleas recovered from the feeding system. Compound 1.1, 1.2, 1.5, 1.6, 1.8, 1.10, 1.12, 1.14, 1.17, 1.18, 1.23-1.25, 1.27-1.30, 1.32-1.35, 1.37-1.39, 1.41, 1.45, 1.47-1.50, 1.55, 1.56, 1.58-1.64, 1.67, 1.69-1.74 showed more than 80% ($EC_{80}$) efficacy at 100 ppm.

2. Activity In Vitro Against *Rhipicephalus sanguineus* (Dog Tick).

A clean adult tick population is used to seed a suitably formatted 96-well plate containing the test substances to be evaluated for antiparasitic activity. Each compound is tested by serial dilution in order to determine its minimal effective dose (MED). Ticks are left in contact with the test compound for 10 minutes and are then incubated at 28° C. and 80% relative humidity for 7 days, during which the test compound's effect is monitored. Acaricidal activity is confirmed if adult ticks are dead.

In this test the following examples showed more than 80% ($EC_{80}$) efficacy at 640 ppm: 1.1, 1.5, 1.6, 1.14, 1.17, 1.18, 1.27-1.30, 1.33-1.35, 1.45, 1.55, 1.56, 1.59-1.61, 1.63, 1.74.

3. Activity In Vivo Against *Rhipicephalus sanguineus* Nymphs on Mongolian Gerbils (*Meriones unguiculatus*) (Spray Application)

On day 0, gerbils are treated with the test compound at a given dose by spray application. On day +1, the animals are infested with nymphs of *R. sangineus*. Ticks are left on the animals until full repletion. Seven days after infestation nymphs dropped off fully engorged are collected and counted. Efficacy in killing is expressed as a tick number reduction in comparison with a placebo treated group using the Abbot's formula.

Results of some compounds from Table 1 are shown in Table 2

| Compound | Dose (mg/kg) | Efficacy (%) |
|---|---|---|
| 1.1 | 100 | 85 |
| 1.27 | 100 | 79 |
| 1.29 | 100 | 86 |
| 1.34 | 32 | 75 |
| 1.61 | 100 | 96 |
| 1.63 | 10 | 74 |

The invention claimed is:

1. A compound of formula (I)

including geometric and stereoisomers, N-oxides, and salts thereof, wherein $A_1, A_2, A_3, A_4, A_5$ and $A_6$ are each independently selected from the group consisting of $CR_3'$ and N;

n is an integer from 0 to 4;

$B_1, B_2$ and $B_3$ are each independently selected from the group consisting of $CR_2'$ and N;

each $R_2'$ is independently of the other H or $R_2$; each $R_3'$ is independently of the other H or $R_3$;

$R_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently selected from $R_4$;

each $R_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_2$-$C_6$ alkoxycarbonyl, cyano (—CN) or nitro (—$NO_2$);

each $R_3$ is independently halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$ alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$-alkylamino, $C_1$-$C_6$-alkoxycarbonyl, —CN or —$NO_2$;

$R_4$ is halogen, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, —CN or —$NO_2$;

Q is a 5- or 6-membered heterocyclic ring, or a $C_6$-$C_{10}$-carbocyclic ring system or a 8-, 9- or 10-membered fused hetero-bicyclic ring system, each of them being unsubstituted or substituted with one or more substituents independently selected from halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_3$-$C_6$-cycloalkoxy, $C_1$-$C_6$-haloalkoxy, $C_2$-$C_6$-alkenyl, $C_2$-$C_6$-haloalkenyl, $C_1$-$C_6$- alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —CN, —NO$_2$, amino, N-mono- or N,N-di-$C_1$-$C_6$-alkylamino, CO$_2$H, $C_1$-$C_6$-alkoxycarbonyl, sulfonamido, N-mono- or N,N,di-$C_1$-$C_6$-alkylsulfonamido, CONH$_2$, N-mono- or N,N-di-$C_1$-$C_6$-alkylaminocarbonyl, N-mono- or N,N,di-$C_1$-$C_6$-haloalkylaminocarbonyl, N—$C_1$-$C_2$-haloalkylaminocarbonyl-$C_1$-$C_2$-alkylaminocarbonyl, $C_1$-$C_6$-alkylcarbonylamino, $C_2$-$C_6$-alkanoyl, $C_2$-$C_6$-haloalkanoyl, CH$_2$R$_5$, a group C(O)N=CHN(CH$_3$)$_2$, a group C(O)N=CHNHOCH$_3$, pyrrolidonylcarbonyl, and unsubstituted or halogen-, $C_1$-$C_6$-alkyl-, $C_1$-$C_6$-haloalkyl-, $C_1$-$C_6$-alkoxy-, $C_1$-$C_6$-haloalkoxy-, nitro- or cyano-substituted phenyl, benzyl, phenethyl, pyridyl, pyridinylmethyl, pyrimidinyl, pyrimidinylmethyl, benzoyl or phenoxy; and R$_5$ is CO$_2$H, $C_1$-$C_6$-alkoxycarbonyl, CONH$_2$, N-mono- or N,N,di-$C_1$-$C_6$-alkylaminocarbonyl, N-mono- or N,N,di-$C_1$-$C_6$-haloalkylaminocarbonyl, $C_1$-$C_6$-alkylcarbonylamino, pyridinylaminocarbonyl or tetrahydrofuranyl.

2. A compound of formula (I) according to claim 1, wherein
A$_1$, A$_2$, A$_3$, A$_4$, A$_5$ and A$_6$ are each independently selected from the group consisting of CR$_3$' and N;
n is an integer from 0 to 4;
B$_1$, B$_2$ and B$_3$ are each independently selected from the group consisting of CR$_2$' and N;
each R$_2$' is independently of the other H or R$_2$;
each R$_3$' is independently of the other H or R$_3$;
R$_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently selected from R$_4$;
each R$_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_2$-$C_6$-alkoxycarbonyl, cyano (—CN) or nitro (—NO$_2$);
each R$_3$ is independently halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$ alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$-alkylamino, $C_2$-$C_6$-alkoxycarbonyl, —CN or —NO$_2$;
R$_4$ is halogen, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, —CN or —NO$_2$; and
Q is a 5- or 6-membered heterocyclic ring, or a $C_6$-$C_{10}$-carbocyclic ring system or a 8-, 9- or 10-membered fused hetero-bicyclic ring system, each of them being unsubstituted or substituted with one or more substituents independently selected from halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —CN, —NO$_2$, amino, N-mono- or N,N-di-$C_1$-$C_6$-alkylamino, $C_2$-$C_6$-alkoxycarbonyl, sulfonamido, N-mono- or N,N,di-$C_1$-$C_4$-alkylsulfonamido, N-mono- or N,N-di-$C_1$-$C_6$-alkylcarbonylamino, $C_2$-$C_6$-alkanoyl and unsubstituted or halogen-, $C_1$-$C_6$-alkyl-, $C_1$-$C_6$-haloalkyl-, $C_1$-$C_6$-alkoxy-, $C_1$-$C_6$-haloalkoxy-, nitro- or cyano-substituted phenyl, benzyl, benzoyl or phenoxy.

3. A compound according to claim 1 of formula (I), wherein B$_1$, B$_2$ and B$_3$ are each CR$_2$'.

4. A compound according to claim 1, wherein A$_1$, A$_2$, A$_3$, A$_4$, A$_5$ and A$_6$ are each CH.

5. A compound according to claim 1, wherein R$_1$ is $C_1$-$C_3$-haloalkyl.

6. A compound according to claim 1 of formula

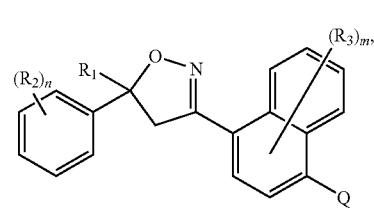

(Ia)

wherein R$_1$, R$_2$, R$_3$, Q and n are as defined in claim 1, and m is an integer from 0 to 4.

7. A compound according to claim 1, wherein Q is a 5- or 6-membered heterocyclic ring having from 1 to 4 same or different heteroatoms selected from the group consisting of N, O and S, which is further unsubstituted or substituted by one or more substituents selected from the group consisting of $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, —CN, —NO$_2$, $C_1$-$C_4$-alkoxycarbonyl, sulfonamido, N-mono- or N,N-di-$C_1$-$C_4$-alkylcarbonylamino, $C_2$-$C_3$-alkanoyl and unsubstituted or halogen- or $C_1$-$C_4$-alkyl-substituted phenyl, benzyl, benzoyl and phenoxy.

8. A compound according to claim 1, wherein Q is a radical of formula

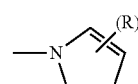

Q-5

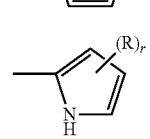

Q-6

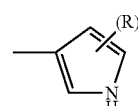

Q-7

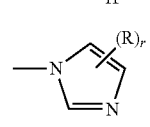

Q-14

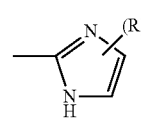

Q-15

-continued

Q-16 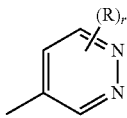

Q-17 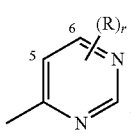

Q-24

Q-26

Q-30

Q-31

Q-32

Q-33

Q-34

Q-43

Q-47

Q-49

Q-50

Q-52 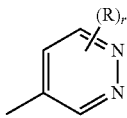

Q-54 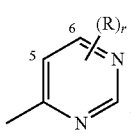

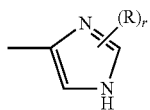
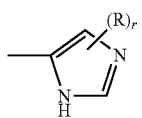
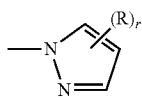
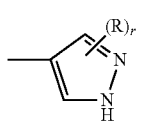
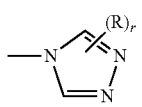
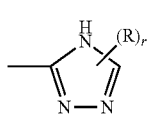
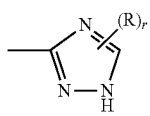
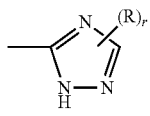
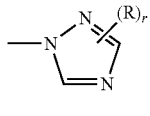
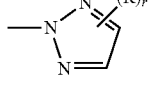
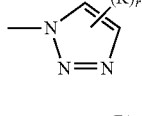
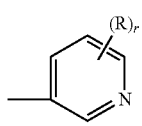
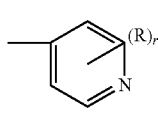

wherein r is an integer from 0 to 3 and R is independently selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$, and $C_1$-$C_4$-alkoxycarbonyl.

9. A compound according to claim 8, wherein Q is the radical Q-34, Q-43 or Q-47, wherein r is in each case 0.

10. A compound of formula (Ia) according to claim 6, wherein n is an integer from 1 to 3, $R_1$ is $C_1$-$C_3$-haloalkyl, each $R_2$ and $R_3$ is independently selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN and —NO$_2$, m is an integer from 0 to 2, and Q is either (i) phenyl, which is unsubstituted or substituted by 1 to 3, same or different substituents selected from the group consisting of halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$, and unsubstituted or halogen-, $C_1$-$C_2$-alkyl-, $C_1$-$C_2$-haloalkyl-, $C_1$-$C_2$-alkoxy-, $C_1$-$C_2$-haloalkoxy-, —CN and —NO$_2$-substituted phenyl or phenoxy, or is (ii) a 5- or 6-membered heterocyclic ring having from 1 to 3 same or different heteroatoms selected from the group consisting of N, O and S, which is further unsubstituted or substituted by halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$ or $C_1$-$C_4$-alkoxycarbonyl, or is (iii) a fused hetero-bicyclic ring system comprising a 5- or 6-membered heterocyclic ring having from 1 to 3 same or different heteroatoms selected from the group consisting of N, O and S, to which is attached an annulated ring, and which is further unsubstituted or substituted by halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, —CN, —NO$_2$ or $C_1$-$C_4$-alkoxycarbonyl.

11. A compound of formula (Ia) according to claim 6, wherein n is an integer from 1 to 3, $R_1$ is CF$_3$, each $R_2$ is independently selected from the group consisting of halogen, $C_1$-$C_2$-haloalkyl, $C_1$-$C_2$-haloalkoxy and —CN, m is 0 and Q is either (ii) a 5- or 6-membered heteroaromatic ring selected from the group consisting of the radicals given in claim 7, or is (iii) a fused hetero-bicyclic ring system selected from the group consisting of the radicals

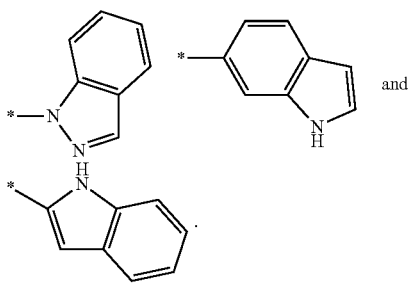 and

12. A compound of formula (Ia) according to claim 6, wherein n is an integer from 1 to 3, $R_1$ is $CF_3$, each $R_2$ is independently selected from the group consisting of halogen, $C_1$-$C_2$-haloalkyl, $C_1$-$C_2$-haloalkoxy and —CN, m is 0 and Q is a radical

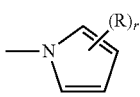 Q-5

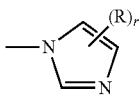 Q-14

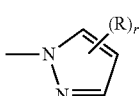 Q-24

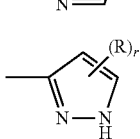 Q-25

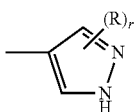 Q-26

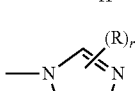 Q-30

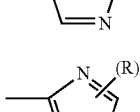 Q-32

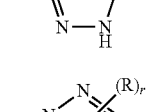 Q-34

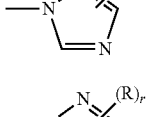 Q-43

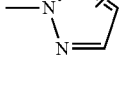

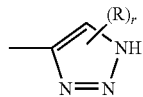 Q-44

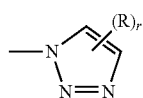 Q-47

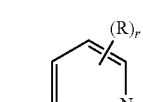 Q-49

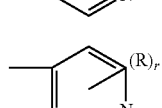 Q-50

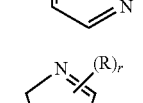 Q-75 wherein r is an integer of 0 or 1, and R is independently selected from the group consisting of $C_1$-$C_2$-alkyl, halo-$C_1$-$C_2$-alkyl, halo-$C_1$-$C_2$-alkylcarbonyl, cyano, $C_1$-$C_4$-alkoxycarbonyl, $C_1$-$C_4$-alkoxycarbonylmethyl, carboxy-$C_1$-$C_2$-alkyl, aminocarbonyl, N-mono- or N,N-di-$C_1$-$C_2$-alkylaminocarbonyl, halo-$C_1$-$C_2$-alkylaminocarbonylmethyl, halo-$C_1$-$C_2$-alkylaminocarbonylmethylaminocarbonyl, halovinyl, —C(O)N=CHN(CH_3)_2, —C(O)N=CHNHOCH_3, unsubstituted or halogen- or $C_1$-$C_2$-alkoxy-substituted phenyl, benzyl and phenylethyl, unsubstituted and halogen-substituted 2-, 3- and 4-pyridyl and pyridylmethyl, pyridylcarbonylaminomethyl, pyrrolidinecarbonyl, and 2-tetrahydrofuranylmethyl.

13. A compound according to claim 5, wherein $R_1$ is $CF_3$.

14. A compound according to claim 7, wherein Q is a 5- or 6-membered heterocyclic ring having from 1 to 3 same or different heteroatoms.

15. A compound according to claim 10, wherein m is 0.

16. A compound according to claim 10, wherein Q is phenyl, which is substituted by 1 or 2 same or different substituents.

17. A compound according to claim 12, wherein Q is the radical Q-24, Q-26, Q-30, Q-32, Q-34, Q-44 or Q-47.

18. Composition for the control of parasites, comprising as active ingredient at least one compound of the formula (I) according to claim 1, in addition to a carrier and/or a dispersant.

19. Method of controlling parasites in and on warm-blooded animals, which comprises applying to the animals a pharmaceutical effective amount of at least one compound of formula (I) according to claim 1.

* * * * *